United States Patent
Brasola et al.

(10) Patent No.: US 10,590,133 B2
(45) Date of Patent: *Mar. 17, 2020

(54) DIMER IMPURITIES OF APIXABAN AND METHOD TO REMOVE THEM

(71) Applicant: F.I.S.-FABBRICA ITALIANA SINTETICI S.P.A., Montecchio Maggiore (VI) (IT)

(72) Inventors: Elena Brasola, Saccolongo (IT); Filippo Tomasi, Brogliano (IT); Loris Peruzzi, Lonigo (IT)

(73) Assignee: F.I.S.-FABBRICA ITALIANA SINTETICI S.P.A., Montecchio Maggiore (VI) (IT)

(*) Notice: Subject to any disclaimer, the term of this patent is extended or adjusted under 35 U.S.C. 154(b) by 0 days.

This patent is subject to a terminal disclaimer.

(21) Appl. No.: 16/456,714

(22) Filed: Jun. 28, 2019

(65) Prior Publication Data

US 2019/0367509 A1  Dec. 5, 2019

Related U.S. Application Data

(62) Division of application No. 15/561,285, filed as application No. PCT/EP2016/067083 on Jul. 18, 2016, now Pat. No. 10,385,049.

(30) Foreign Application Priority Data

Jul. 20, 2015 (EP) ..................... 15177517

(51) Int. Cl.
| | |
|---|---|
| C07D 471/04 | (2006.01) |
| B01D 11/02 | (2006.01) |
| C07B 63/00 | (2006.01) |
| C07D 413/04 | (2006.01) |
| C07D 413/14 | (2006.01) |
| G01N 30/36 | (2006.01) |
| G01N 30/72 | (2006.01) |
| G01N 30/02 | (2006.01) |

(52) U.S. Cl.
CPC ............ *C07D 471/04* (2013.01); *B01D 11/02* (2013.01); *C07B 63/00* (2013.01); *C07D 413/04* (2013.01); *C07D 413/14* (2013.01); *G01N 30/36* (2013.01); *G01N 30/7233* (2013.01); *G01N 2030/027* (2013.01)

(58) Field of Classification Search
CPC ....................................... C07D 471/04
USPC ........................................... 546/118
See application file for complete search history.

(56) References Cited

U.S. PATENT DOCUMENTS 10,385,049 B2 * 8/2019 Brasola ............... C07D 413/04

FOREIGN PATENT DOCUMENTS

| CN | 103626689 A | 3/2014 |
|---|---|---|
| CN | 103626759 A | 3/2014 |
| CN | 103739541 A | 4/2014 |
| CN | 104030972 A | 9/2014 |
| WO | 03049681 A2 | 6/2003 |
| WO | 2007001385 A2 | 1/2007 |
| WO | 2014108919 A2 | 7/2014 |
| WO | 2015018289 A1 | 2/2015 |

OTHER PUBLICATIONS

Raman, Journal of Pharmaceutical and Biomedical Analysis, vol. 55, Issue 4, 2011, pp. 662-667.*
Gupta, International Research Journal of Pharmaceutical & Applied Sciences (2012), 2(4), 17-25.*
Venugopal, Journal of Pharmaceutical and Biomedical Analysis (2012), 70, 592-597.*
Reddy, Journal of Chemical and Pharmaceutical Research (2012), 4(7), 3659-3664.*
Armstrong, Lipidomics, vol. 1: Methods and Protocols, Humana Press, 2009. Lundström, Chpater 8, pp. 161-188.*
Prabhune, Sci Pharm. 2014; 82: 777-785.*
Anom. IP.com Journal (2012), 12(3A), 34 (both specific for Apixaban).*
International Search Report and Written Opinion for International Application No. PCT/EP2016/067083 (16 Pages) (dated Nov. 14, 2016).

* cited by examiner

*Primary Examiner* — Nizal S Chandrakumar
(74) *Attorney, Agent, or Firm* — Lucas & Mercanti, LLP

(57) ABSTRACT

Object of the present invention are dimer impurities of the active ingredient Apixaban, analytical methods for identifying and/or quantifying them and a synthetic method for removing or limiting said impurities from Apixaban and synthetic precursors thereof.

3 Claims, 3 Drawing Sheets

DIMER IMPURITIES OF APIXABAN AND METHOD TO REMOVE THEM

CROSS-REFERENCE TO RELATED APPLICATION

This application is a divisional of U.S. patent application Ser. No. 15/561,285, filed Sep. 25, 2017, which is a 371 of PCT/EP2016/067083, filed Jul. 18, 2016, which claims the benefit of priority from European Patent Application Serial No. 15177517.8, filed Jul. 20, 2015, the contents of each of which are incorporated herein by reference.

TECHNICAL FIELD

The present invention relates to impurities of the active ingredient Apixaban, which may be produced during the synthesis of Apixaban, to methods for identifying and/or quantifying such impurities and to a synthetic method for removing or limiting the presence thereof in Apixaban and its synthetic precursors.

The invention also relates to the use of these dimer impurities in analytical methods.

BACKGROUND ART

Apixaban is an active pharmaceutical ingredient used as anticoagulant for the treatment of venous thromboembolic events. Moreover it has also shown promise in treating acute coronary syndrome (ACS), cerebrovascular ischemia and cancer.

Apixaban having the following chemical formula (I):

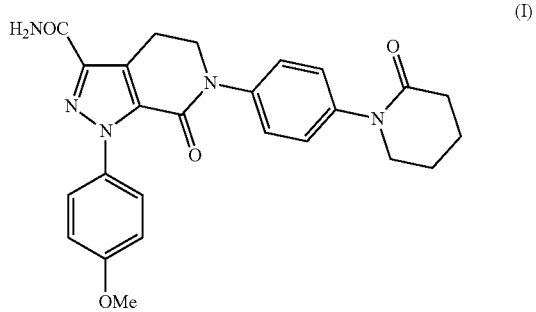 [SMILES: COc1ccc(-n2nc(C(N)=O)c3c2C(=O)N(c2ccc(N4CCCCC4=O)cc2)CC3)cc1]

has chemical name, 1-(4-methoxyphenyl)-7-oxo-6-[4-(2-oxopiperidin-1-yl)phenyl]-4,5-dihydropyrazolo[5,4-c]pyridine-3-carboxamide and CAS RN 503612-47-3.

Several methods for the preparation of Apixaban have been described.

In particular, WO2007/001385 discloses a synthesis on multi-Kilos scale.

Specifically, WO2007/001385 discloses, in the example 6, a process for the preparation of Apixaban by amidation reaction on 10 Kg scale of the Apixaban ethyl ester according to the following reaction scheme:

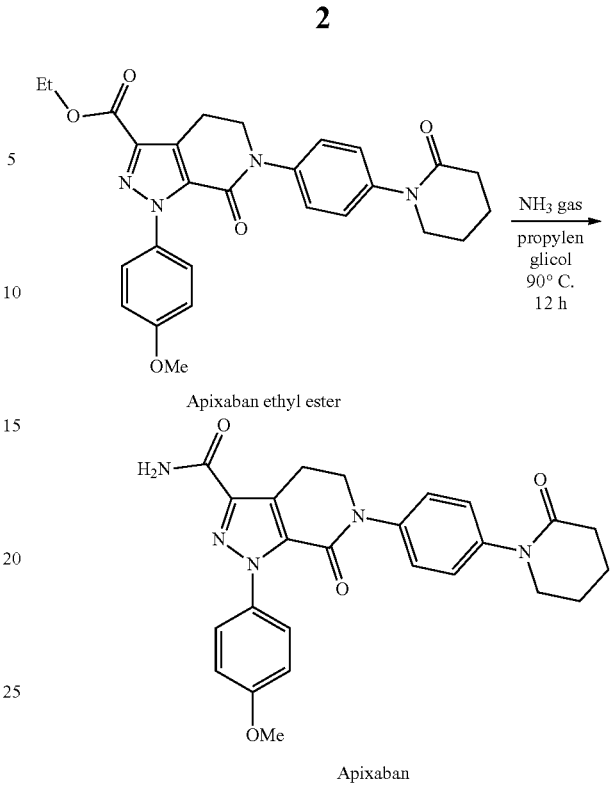

Apixaban ethyl ester

Apixaban

According to said procedure, using anhydrous ammonia in propylene glycol and performing the reaction for at least 12 hours at 90° C., Apixaban was obtained with 94.6% of isolated molar yield.

Synthetic Communications, 43, 72-79, 2013 Jian'an Jing and YafeiJi discloses a cost-effective synthetic strategy to Apixaban as outlined in the scheme 3 at pag. 74 of said publication.

Another method for the preparation of Apixaban is disclosed in WO 03/049681; in particular, in the examples from 54 to 56, is described the route of synthesis for preparing said active pharmaceutical ingredient, starting from compound 10, an intermediate of Apixaban. Specifically in the example 54 in the last section of Part B., 3-Morpholin-4-yl-1-[4-(2-oxo-piperidin-1-yl)-phenyl]-5,6-dihydro-1H-pyridin-2-one (63) is produced by means of a mixture of ammonium hydroxide solution and EtOAc; finally the compound 63 is obtained after a purification by flash column chromatography. Instead, in the Part A of the same example is prepared a different compound, called copper (I), a catalyst, by means of a filtration and following washing with ethanol and then diethyl ether. The obtained copper (I) catalyses the reaction to produce the compound 63, therefore the above mentioned filtration and washing with ethanol and then diethyl ether are not carried out to produce the compound 63, but just to remove copper (I).

A further method to obtain an intermediate of Apixaban is disclosed in CN104030972. In particular in the example 1 is disclosed the process to obtain the compound (I), i.e. an intermediate of Apixaban. Specifically in the step (3) said compound is obtained by means of the addition of water followed by filtration; finally the compound (I) is produced with yield 74.0% and purity higher than 98.5%.

During our laboratory experimentation, it was surprisingly found that many routes of synthesis disclosed in the literature for the preparation of Apixaban provide product contaminated by impurities having high molecular weight.

The presence of said high molecular impurities, especially in amounts higher than 0.10%, is not acceptable in a pharmaceutical active substance such as Apixaban.

SUMMARY OF INVENTION

The problem addressed by the present invention is therefore that of providing an improved process for the preparation of Apixaban which allows the preparation of Apixaban having a low content of impurities having high molecular weight.

This problem is solved by a process for the preparation of Apixaban as outlined in the annexed claims, whose definitions are integral part of the present description.

Particularly, in a first aspect, the present invention provides a process to produce the active ingredient Apixaban substantially free from dimer impurities having the following structure (II) and/or (III):

In a further aspect, the invention provides a method for the determination of the dimer impurities formula (II) and/or formula (III) in Apixaban.

In a yet further aspect, the invention provides the compounds of formula (II), (III), (IV), (V), (VI) and (VII) as novel chemical entities.

In a further aspect, the invention provides the use of the isolated impurity of formula (II), (III), (IV), (V), (VI) and (VII) as a "reference marker" and/or "reference standard" in methods for determining the identity and/or the amount of said impurities in a sample of Apixaban or in its precursors.

DRAWINGS

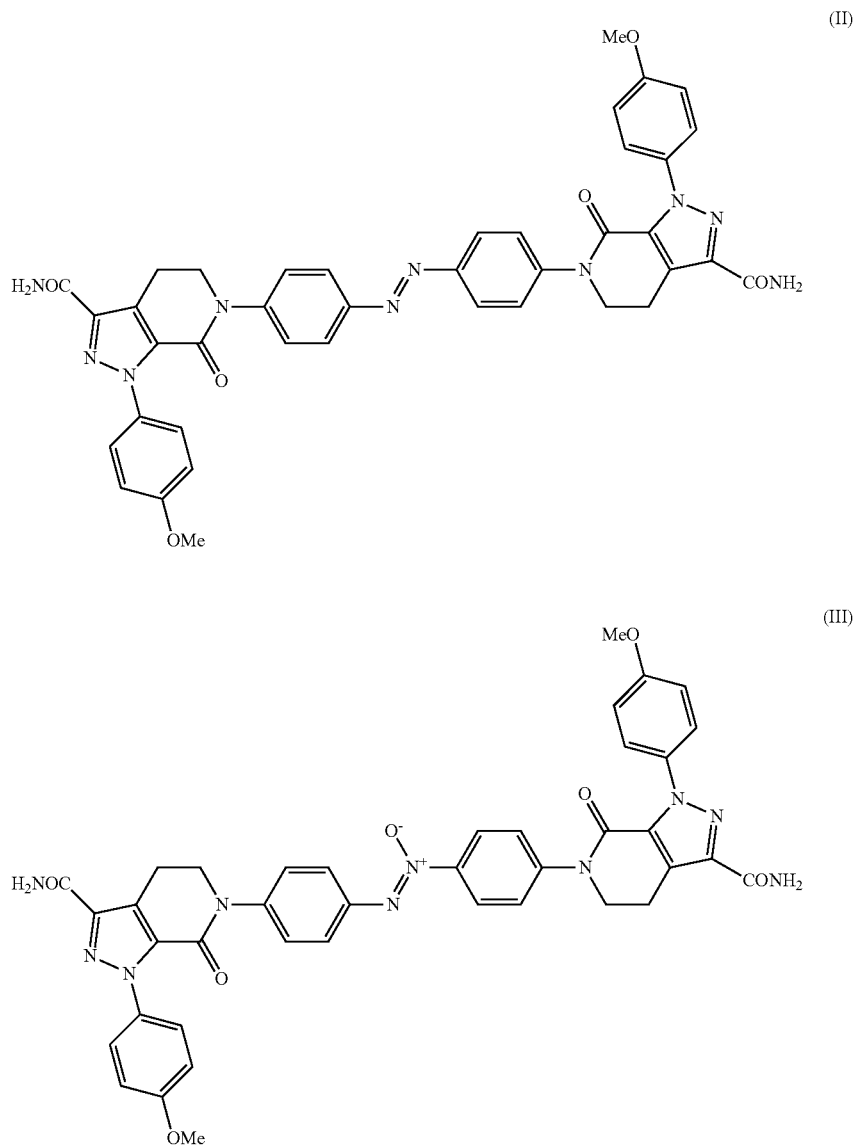

including the carry-over of the impurities through said synthesis in terms of chemical structures and amounts of said impurities, as obtained according to the process comprising the steps from a) to d).

Figure 3:
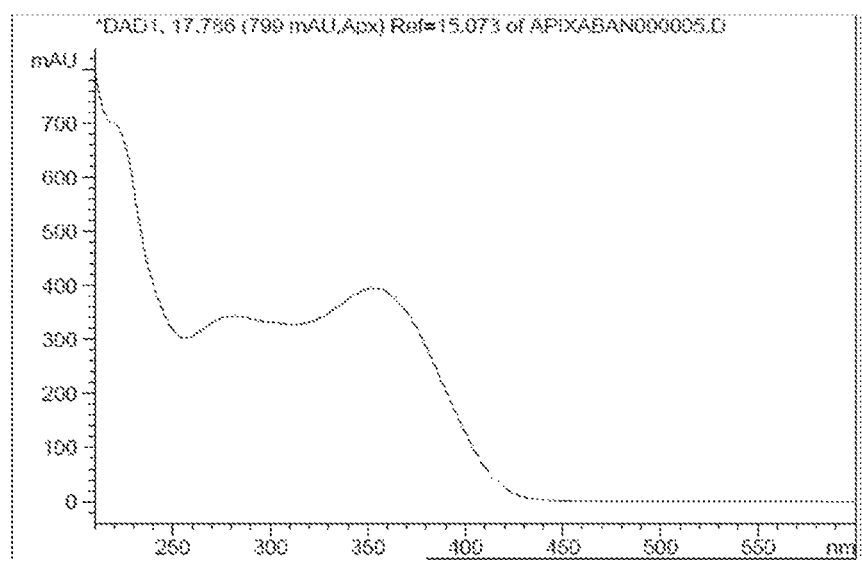

FIG. 3 shows the UV spectrum of the dimer impurity of Apixaban of formula (II) measured by LC-MS.

Figure 4:
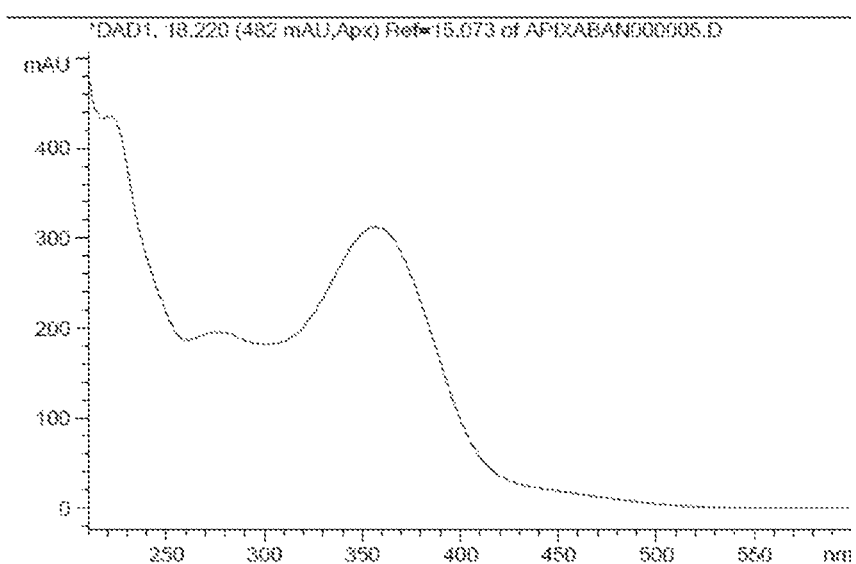

FIG. 4 shows the UV spectrum of the dimer impurity of Apixaban of formula (III) measured by LC-MS.

DESCRIPTION OF EMBODIMENTS

Object of the present invention is a process for the preparation of Apixaban of formula (I):

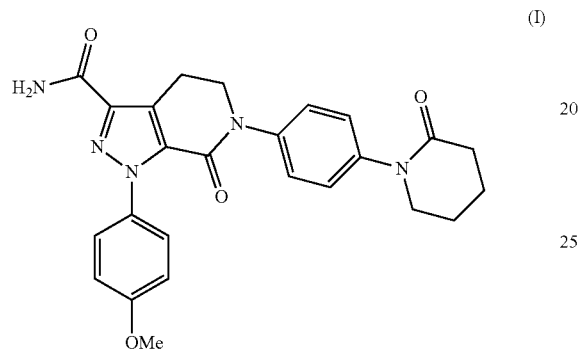

said Apixaban comprising less than 0.10% of the following dimer impurity of Apixaban:

(E)-6,6'-(4,4'-(diazene-1,2-diyl)bis(4,1-phenylene))bis(1-(4-methoxyphenyl)-7-oxo-4,5,6,7-tetrahydro-1H-pyrazolo[3,4-c]pyridine-3-carboxamide), having the following structure (II):

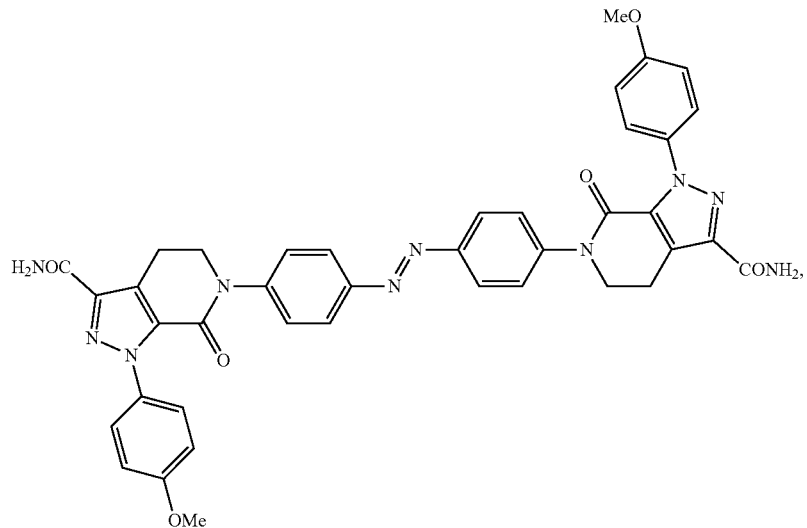

and/or of the dimer impurity of Apixaban:

(Z)-1,2-bis(4-(3-carbamoyl-1-(4-methoxyphenyl)-7-oxo-4,5-dihydro-1H-pyrazolo[3,4-c]pyridin-6(7H)-yl)phenyl)diazene oxide having the following structure (III):

(III)

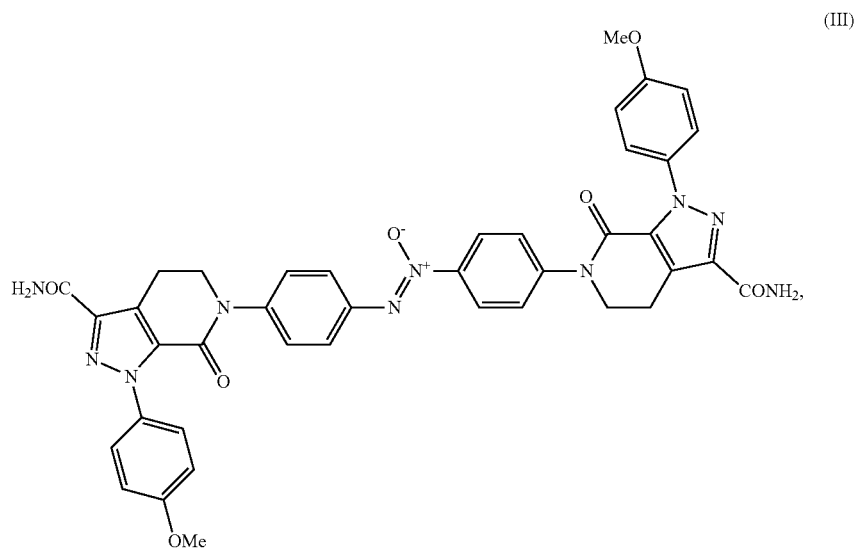

wherein said process comprises the following steps:

a) preparing a solution of 3-morpholino-1-(4-(2-oxopiperidin-1-yl)phenyl)-5,6-dihydropyridin-2(1H)-one of formula (IX)

(IX)

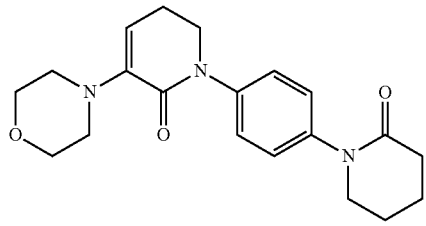

in a mixture of a C1-C3 alcohol and water, b) filtering the solution prepared in the step a) to remove the following dimer impurity:

(E)-1,1'-(4,4'-(diazene-1,2-diyl)bis(4,1-phenylene))bis(3-morpholino-5,6-dihydropyridin-2(1H)-one) of formula (VI) and/or the impurity (Z)-1,2-bis(4-(3-morpholino-2-oxo-5,6-dihydropyridin-1(2H)-yl)phenyl)diazene oxide of formula (VII):

(VI)

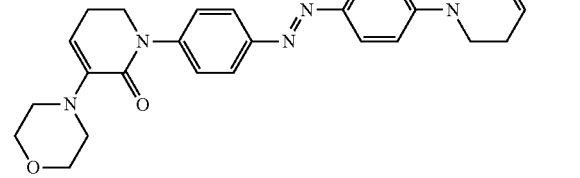

(VII)

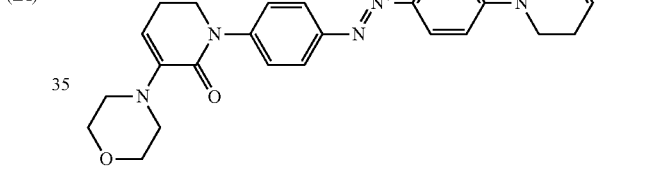

c) obtaining, in the filtrate, a solution comprising the purified compound of formula (IX), d) conversion of the compound of formula (IX) of step c) to Apixaban of formula (I);

or, alternatively, the steps from a) to d) are substituted by the following:

e) preparing a solution of ethyl 1-(4-methoxyphenyl)-7-oxo-6-(4-(2-oxopiperidin-1-yl)phenyl)-4,5,6,7-tetrahydro-1H-pyrazolo[3,4-c]pyridine-3-carboxylate of formula (VIII):

(VIII)

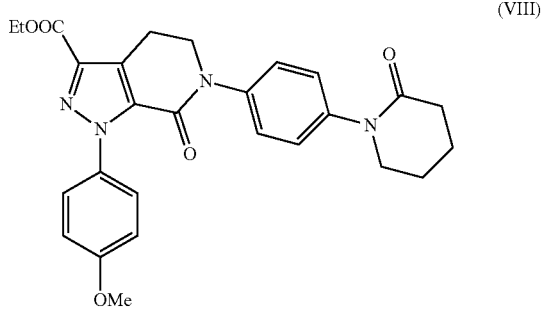 [SMILES: CCOC(=O)c1nn(-c2ccc(OC)cc2)c2c1CCN(c1ccc(N3CCCCC3=O)cc1)C2=O]

in a C1-C4 alcohol, f) filtering the solution prepared in the step e) to remove the following dimer impurity:

(E)-diethyl 6,6'-(4,4'-(diazene-1,2-diyl)bis(4,1-phenylene))bis(1-(4-methoxyphenyl)-7-oxo-4,5,6,7-tetrahydro-1H-pyrazolo[3,4-c]pyridine-3-carboxylate) having the following formula (IV) and/or the impurity (Z)-1,2-bis(4-(3-(ethoxycarbonyl)-1-(4-methoxyphenyl)-7-oxo-4,5-dihydro-1H-pyrazolo[3,4-c]pyridin-6(7H)-yl)phenyl)diazene oxide of formula (V):

remained on the filter indeed does not contain amounts of the product of formula (IX) or (VIII), but contains only the dimer impurities of formula (VI) and (VII) or (IV) and (V) and, optionally, other inorganic filter aids and/or active charcoal.

An advantage of the process of this invention is that allows the preparation of Apixaban and of the precursors

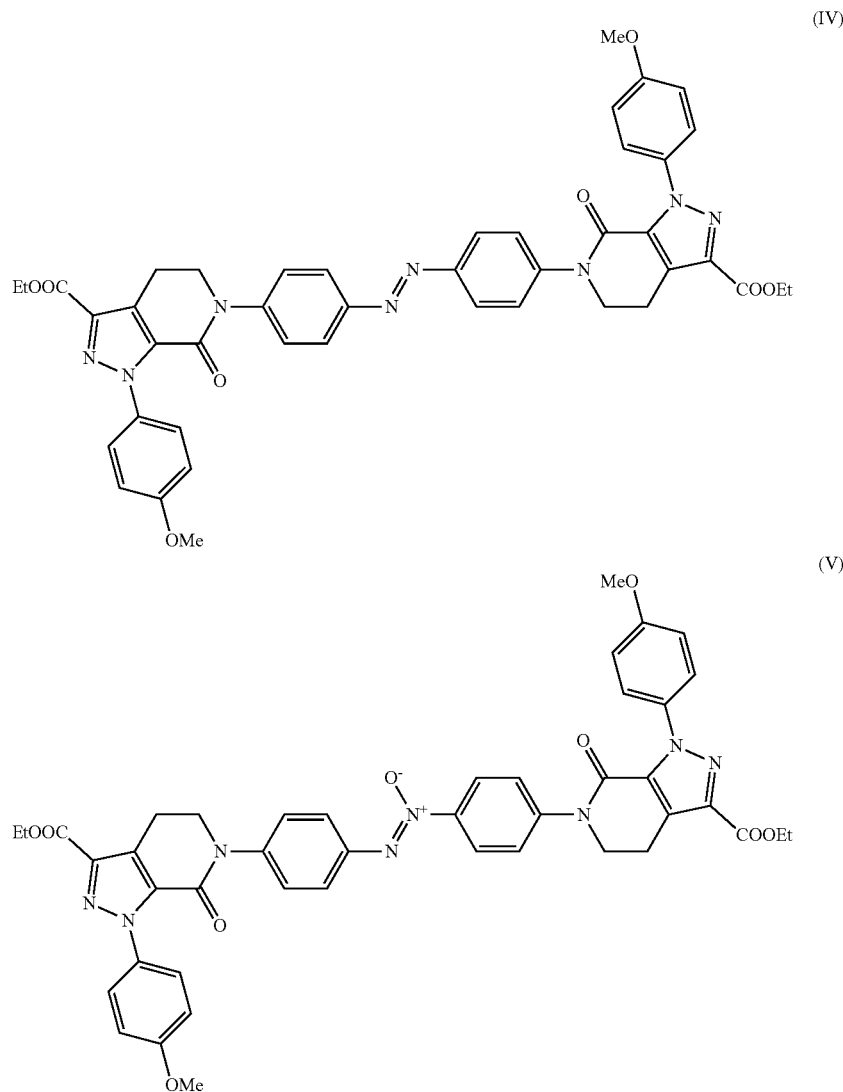

g) obtaining, in the filtrate, a solution comprising the purified compound of formula (VIII), h) optionally, isolating as solid the purified compound of formula (VIII) and the steps from e) to g) are repeated one or more times, i) conversion of the compound of formula (VIII) of step g) or h) to Apixaban of formula (I).

It has been indeed surprisingly found that filtering an aqueous alcoholic solution comprising the compound of formula (IX) and/or an alcoholic solution of the compound of formula (VIII) is possible to remove selectively the related dimer impurities respectively of formula (VI) and (VII), (IV) and (V). Said impurities remain thus as solid on the filter and, meanwhile, all the amount the purified product is collected in the filtered solution. The solid matter thereof of formula (IX) and (VIII) containing less than 0.10% of each dimer impurity respectively of formula (II) and (III), (VI) and (VII), (IV) and (V).

Another very important advantage of the process of the present invention is that said process is very efficient in the reduction of the levels of the dimer impurities and, at the same time, is extremely efficient in removing dimer impurities avoiding any loss of the product, i.e. providing product with an almost quantitative yield. This result is surely better than that achievable by any other recrystallization process wherein, although could be theoretically possible to reach the same reduction of the level of the dimer impurities, the yield of the purified product is surely well lower than the almost quantitative yield obtained by the process of the present invention.

Figure 1:
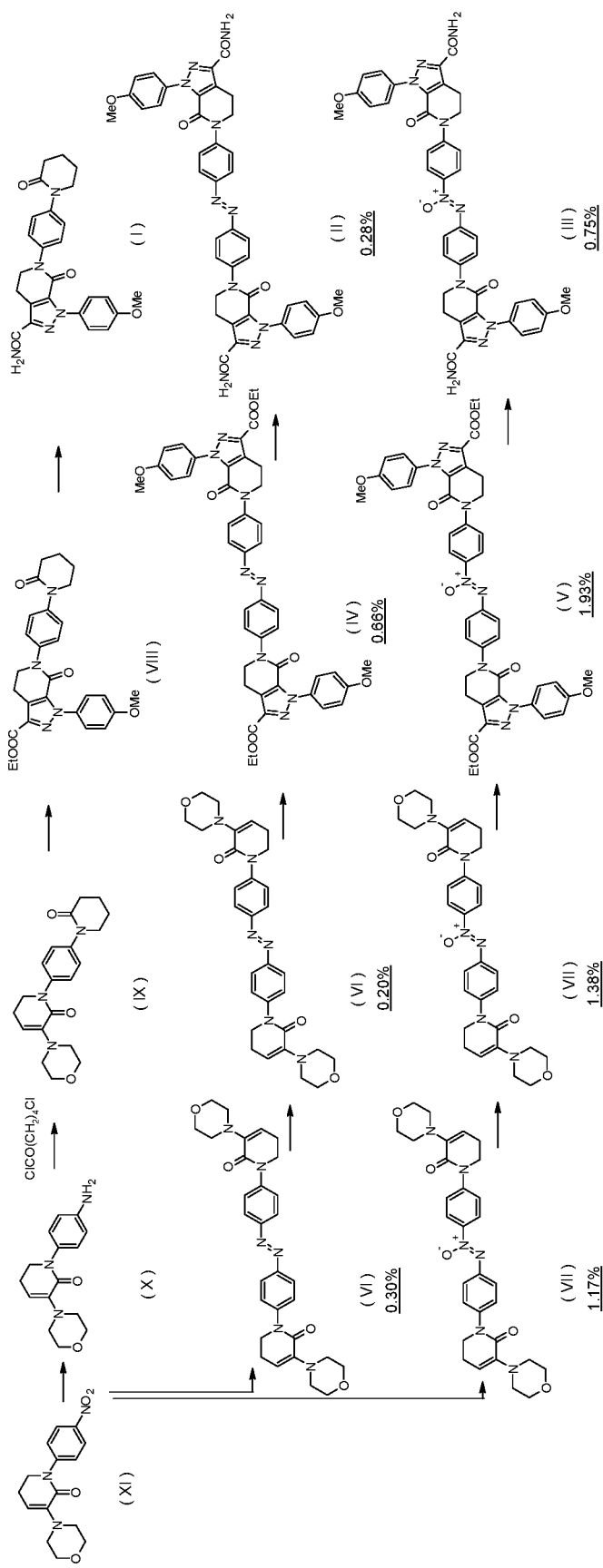
FIG. 1 shows an overall scheme of synthesis of Apixaban, including the carry-over of the impurities through said synthesis in terms of chemical structures and amounts of said impurities, as in the prior art procedure.

Moreover, it has been observed that said dimer impurities, as shown in FIG. 1, are very difficult to be removed, indeed, they are present in each step of the process of synthesis of Apixaban since during the isolation of the intermediates they are not lost, thus arriving to the product Apixaban with an high content of dimer impurities, crossing all the synthetic steps of the process.

Finally, it must be considered that, since these dimer impurities of Apixaban have an high molecular weight, they show high relative retention times at HPLC analysis, or very often, in analytical method directed to the analysis of Apixaban and its relates impurities, such as for example isomer impurities, said dimer impurities are retained by the chromatographic column and, in the most of the cases, they are not eluted, remaining on the head of the column. Therefore, the determination of the presence of said dimer impurities it not evident, and, as consequence, since it is not obvious the determination of the presence of the dimer impurities. The same applies to a method directed to the removal or reduction of said impurities.

The compound of the following formula (IX) can be prepared according to synthetic methods disclosed in Synthetic Communication, 2013, vol. 43, pag. 72-79:

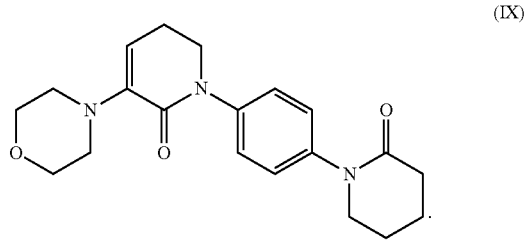 [SMILES: O=C1CCCCN1c1ccc(N2CCC=C(N3CCOCC3)C2=O)cc1]

(IX)

The compound of the following formula (VIII) can be prepared according to the methods in the above mentioned article:

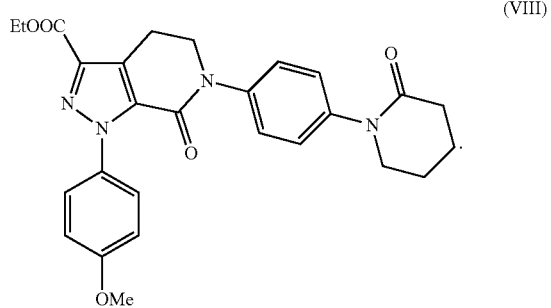 [SMILES: CCOC(=O)c1nn(-c2ccc(OC)cc2)c2c1CCN(c1ccc(N3CCCCC3=O)cc1)C2=O]

(VIII)

The Apixaban prepared according to the process of the present invention comprises less than 0.10% of each of dimer impurities of Apixaban of formula (II) and (III), wherein 0.10% is determined by analysis HPLC A/A %. Said determination can be conveniently carry out using the analytical method described in example 8.

In the step a) of the process of the present invention is prepared a solution of 3-morpholino-1-(4-(2-oxopiperidin-1-yl)phenyl)-5,6-dihydropyridin-2(1H)-one of formula (IX):

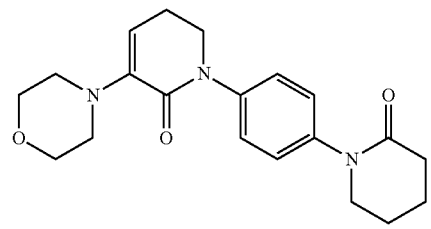

(IX)

in a mixture of a C1-C3 alcohol and water.

Preparing a solution of the compound of formula (IX) means to dissolve the compound of formula (IX), being in solid form, in a mixture of a C1-C3 alcohol and water or, alternatively, dissolve (IX) in a C1-C3 alcohol and then adding water.

Alternatively, the preparation of a solution of the compound of formula (IX) can also be achieved by converting, in a mixture C1-C3 alcohol and water, another compound (i.e. a precursor) into the compound of formula (IX).

Alternatively, the preparation of a solution of the compound of formula (IX) can also be achieved by converting, in a C1-C3 alcohol, another compound (i.e. a precursor) into the compound of formula (IX) and then adding water.

Alternatively, the preparation of a solution of the compound of formula (IX) can also be achieved by converting, in another solvent, another compound (i.e. a precursor) into the compound of formula (IX) and then switching the solvent with a mixture C1-C3 alcohol and water, or, with a C1-C3 alcohol and then adding water.

According to a preferred embodiment, another compound (i.e. a precursor) can be, for example, the compound of formula (X):

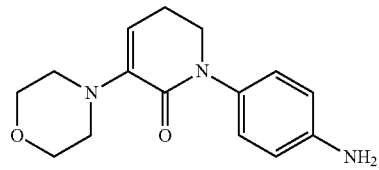

(X)

According to a preferred embodiment, the conversion of the compound of formula (X) to the compound of formula (IX) is carried out by means of reaction with chlorovaleryl-chloride.

According to a preferred embodiment, in the mixture of C1-C3 alcohol and water the C1-C3 alcohol is ethanol.

According to a preferred embodiment, the switch of the solvent is done with a C1-C3 alcohol and then water is added. More preferably, the switch of the solvent is done with ethanol and then water is added.

The solution of 3-morpholino-1-(4-(2-oxopiperidin-1-yl)phenyl)-5,6-dihydropyridin-2(1H)-one of formula (IX):

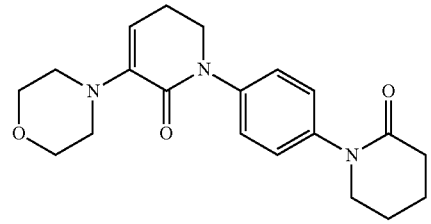

(IX)

in a mixture of a C1-C3 alcohol and water, prepared in the step a) of the process of the present invention is an opalescent solution or a micro-suspension or a suspension of little amount of solid material, typically said amount of insoluble material is less than 5% by weight of weight of the compound of formula (IX). In said solution indeed, the dimer impurities of formula (VI) and (VII) remain as insoluble solids, thus proving an opalescent aspect to the solution of the compound (IX) or a micro-suspension or a suspension of little amount of solid material constituted by dimer impurities of formula (VI) and (VII).

The compound of formula (IX) is instead completely solubilized in the solution of a C1-C3 alcohol and water.

In the mixture of a C1-C3 alcohol and water, a C1-C3 alcohol is a monoalcohol solvent chosen between methanol, ethanol and n-propanol or isopropanol.

In the step a) of the process of the present invention, the amount of C1-C3 alcohol is from 2 to 30 volumes compared to the compound of formula (IX).

Volumes means volume of solvent per unit of product, thus, for example, 1 volume is 1 Liter per 1 Kilo, or 1 mL for 1 gram, or 1 microliter per 1 milligram. Thus, 10 volumes means for example 10 liters per 1 Kilogram of substance, in this case, the compound of formula (IX).

According to a preferred embodiment of the process of the present invention, in the step a), the amount of C1-C3 alcohol is from 5 to 20 volumes compared to the compound of formula (IX).

According to a more preferred embodiment of the process of the present invention, in the step a), the amount of C1-C3 alcohol is from 10 to 15 volumes compared to the compound of formula (IX), again more preferably, the volume is about 13 volumes.

In the step a) of the process of the present invention, the amount of water is from 0.5 to 20 volumes compared to the compound of formula (IX).

According to a preferred embodiment of the process of the present invention, in the step a), the amount of water is from 1 to 15 volumes compared to the compound of formula (IX).

According to a more preferred embodiment of the process of the present invention, in the step a), the amount of water is from 7 to 13 volumes compared to the compound of formula (IX), more preferably is about 10 volumes.

According to a preferred embodiment of the process of the present invention, in the step a) the amount of C1-C3 alcohol is from 5 to 20 volumes and the amount of water is from 1 to 15 volumes, both compared to the compound of formula (IX).

According to a more preferred embodiment of the process of the present invention, in the step a) the amount of C1-C3 alcohol is from 10 to 15 volumes and the amount of water is from 7 to 13 volumes, both compared to the compound of formula (IX), again more preferably, the amount of C1-C3 alcohol is about 13 volumes and the amount of water is about 10 volumes, both compared to the compound of formula (IX).

In particular, in the step a), the ratio by volume between the amount of water and the amount of C1-C3 alcohol in the mixture is comprised in a range between 2.4% and 80% (v/v %) of water in said mixture of water and C1-C3 alcohol, preferably in a range between 6.25% and 60% (v/v %) of water in the above mentioned mixture of water and C1-C3 alcohol, and more preferably in a range between 35% and 50% (v/v %) of water in beforehand mentioned mixture of water and C1-C3 alcohol.

According to a preferred embodiment of the process of the present invention, in the step a) the C1-C3 alcohol is ethanol.

According to a more preferred embodiment of the process of the present invention, in the step a) the amount of Ethanol is from 10 to 15 volumes and the amount of water is from 7 to 13 volumes, both compared to the compound of formula (IX), again more preferably, the amount of ethanol is about 13 volumes and the amount of water is about 10 volumes, both compared to the compound of formula (IX).

The step a) of the process of the present invention can be carried out at a temperature comprised between 20° C. and 120° C.

According to a preferred embodiment of the process of the present invention, the step a) is carried out at a temperature comprised between 30° C. to 50° C.

According to a preferred embodiment of the process of the present invention, the step a) is carried out at a temperature comprised between 40° C. to 45° C.

According to a more preferred embodiment of the process of the present invention, the step a) is carried out at temperature comprised between 30° C. to 50° C. and the amount of ethanol is from 10 to 15 volumes and the amount of water is from 7 to 13 volumes, both compared to the compound of formula (IX).

More preferably, the step a) is carried out at temperature comprised between 40° C. to 45° C. and the amount of ethanol is about 13 volumes and the amount of water is about 10 volumes, both compared to the compound of formula (IX).

According to a preferred embodiment of the process of the present invention, in the step a) is further added a filter aid and/or activated charcoal.

After the solution of step a) is prepared, in the step b), said solution is filtered to remove the dimer impurities of formula (VI) and (VII).

The solution prepared in the step a) can be filtered on filter paper, or a panel of filter paper or on a panel of dicalite.

According to a preferred embodiment of the process of the present invention, in step b) is carried out by means of a dicalite panel.

The step b) of the process of the present invention can be carried out at a temperature comprised between 20° C. and 120° C.

According to a preferred embodiment of the process of the present invention, the step b) is carried out at a temperature comprised between 30° C. to 50° C.

According to a preferred embodiment of the process of the present invention, the step b) is carried out at a temperature comprised between 40° C. to 45° C.

According to a preferred embodiment of the process of the present invention, in the step b), the filter is further washed with the C1-C3 alcohol solvent pre-heated at same temperature of the filtration already carried out.

The insoluble impurities of formula (VI) and (VII) remain as solid material on the filter and, in the case where in the step a) is further added a filter aid and/or activated charcoal or in the step b) the filtration is performed on a dicalite panel, they are comprised on the filter cake.

In the step c) is obtained, in the filtrate, a solution comprising the purified compound of formula (IX).

The compound of formula (IX) obtained in step c) is converted, in the step d), to Apixaban of formula (I) according to the known prior art methods such as those disclosed in Synthetic Communications, 43; 72-79, 2013 or preferably the method disclosed in WO2007/001385.

According to an alternative method of the present invention, always based on the same inventive concept, the steps from a) to d) above described are substituted by the following steps form e) to i).

In the step e) is prepared a solution of ethyl 1-(4-methoxyphenyl)-7-oxo-6-(4-(2-oxopiperidin-1-yl)phenyl)-4,5,6,7-tetrahydro-1H-pyrazolo[3,4-c]pyridine-3-carboxylate of formula (VIII):

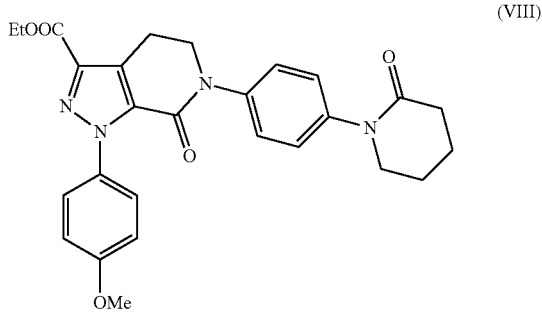 [SMILES: CCOC(=O)c1nn(-c2ccc(OC)cc2)c2c1CCN(c1ccc(N3CCCCC3=O)cc1)C2=O]

in a C1-C4 alcohol.

The preparation of said solution of compound (VIII) in the step e) can be carried out similarly to that described for the compound of formula (IX) in the step a), including all the variants already described.

The C1-C4 alcohol is selected in the group of monoalcohols consisting in methanol, ethanol, n-propanol, isopropanol, n-butanol, isobutanol, sec-butanol and tert-butanol.

According to a preferred embodiment of the process of the present invention, in the step e) the C1-C4 alcohol is ethanol.

In the step e) of the process of the present invention, the amount of C1-C4 alcohol is from 3 to 20 volumes compared to the compound of formula (VIII).

According to a preferred embodiment of the process of the present invention, in the step e) the amount of C1-C4 alcohol is from 5 to 15 volumes, more preferably is about 10 volumes, compared to the compound of formula (VIII).

According to the process of the present invention, the step e) is carried out at a temperature comprised between 40° C. and the boiling point of the alcohol.

According to a more preferred embodiment of the process of the present invention, the step e) is carried out at the temperature of boiling point of the alcohol, i.e. at reflux temperature.

According to a preferred embodiment of the process of the present invention, the step e) is carried out with 10 volumes of ethanol compared to the compound of formula (VIII), at the boiling point of the ethanol.

According to a preferred embodiment of the process of the present invention, in the step e) is further added a filter aid and/or activated charcoal.

According to a more preferred embodiment of the process of the present invention, in the step e) is further added activated charcoal.

After the solution of step e) is prepared, in the step f), said solution is filtered to remove the dimer impurity of formula (IV) and/or of formula (V).

The solution prepared in the step e) can be filtered on filter paper, or a panel of filter paper or on a panel of dicalite.

The step f) of the process of the present invention can be carried out at a temperature comprised between 40° C. and the boiling point of the alcohol.

According to a preferred embodiment of the process of the present invention, the step f), is carried out at the boiling point of the alcohol.

According to a preferred embodiment of the process of the present invention, the step f), the filter is further washed with the C1-C4 alcohol solvent pre-heated at same temperature of the filtration already carried out.

The insoluble impurities of formula (IV) and (V) remain as solid material in the filter and, in the case where in the step e) is further added a filter aid and/or activated charcoal or in the step f) the filtration is performed on a dicalite panel, they are comprised on the filter cake.

Optionally, especially in the case where the residual impurities of formula (IV) and (V) in the purified compound of formula (VIII) are still higher than 0.10%, in the step h), the purified compound of formula (VIII) can be therefore isolated as solid and can be further purified repeating the steps from e) to g), one or more times.

The purified compound of formula (VIII) obtained in step g) or h) is converted, in the step i), to Apixaban of formula (I) according to the known prior art methods such as those disclosed in Synthetic Communications, 43; 72-79, 2013 or in WO2007/001385.

According to a preferred embodiment of the process of the present invention, Apixaban comprises less than 0.10% of the following dimer impurity of Apixaban: (Z)-1,2-bis(4-(3-carbamoyl-1-(4-methoxyphenyl)-7-oxo-4,5-dihydro-1H-pyrazolo[3,4-c]pyridin-6(7H)-yl)phenyl)diazene oxide having the following formula (III):

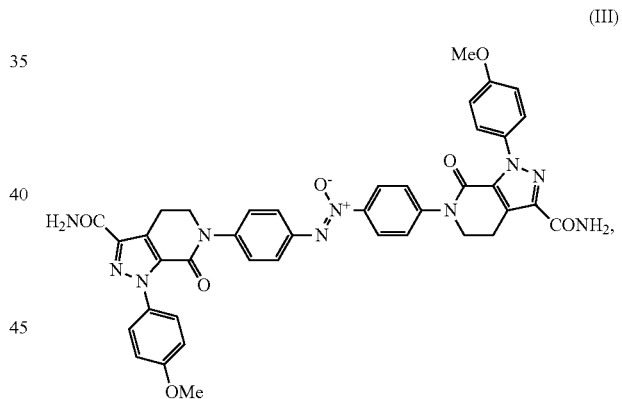

wherein in the step b) is removed the dimer impurity of formula (VII), or alternatively in the step f) is removed the impurity of formula (V).

Dimer impurity of formula (III) and precursors thereof have a particular structure, since they bear electronic charges making them more polar, hence they are less soluble in an organic solvent, and, at the same time, they are thus more easily removed in the step b) or f) of the present invention.

According to a preferred embodiment of the process of the present invention, Apixaban comprises less than 0.01% of dimer impurity of formula (II) and/or of formula (III).

According to a preferred embodiment of the process of the present invention, Apixaban contains from 0.00% to 0.02% of dimer impurity of formula (II) and/or of formula (III), as determined by HPLC A/A %, and said process comprises the conversion of the compound of formula (IX) to Apixaban, and wherein said compound of formula (IX) comprises an amount of the dimer impurities of formula (VI)

and/or formula (VII) comprised between 0.1% and 2%, as determined by HPLC A/A %.

According to a preferred embodiment of the process of the present invention, Apixaban contains from 0.02% to 0.10% of dimer impurity of formula (II) and/or of formula (III), as determined by HPLC A/A %, and said process comprises the conversion of the compound of formula (IX) to Apixaban, and wherein said compound of formula (IX) comprises an amount of the dimer impurities of formula (VI) and/or formula (VII) comprised between 2% and 5%, as determined by HPLC A/A %.

Specifically, starting from the compound of formula (IX), comprising an amount from 2% and 5% of the dimer impurities of formula (VI) and/or formula (VII), following the process of the invention comprising the step a), b), c) and d), as beforehand described, Apixaban containing from 0.02% to 0.10% of dimer impurity of formula (II) and/or of formula (III) is obtained.

According to a preferred embodiment of the process of the present invention, Apixaban obtained in the step d) or in the step i) has N-1 form.

Apixaban N-1 form means Apixaban having the polymorphic form, named N-1, a solid form which is well characterized and produced, in examples of EP3009435 said form is defined to be the thermodynamically stable form of Apixaban. Furthermore Apixaban form N-1 was characterized, in particular in the experimental section, example 3, of said application by several techniques, as FT-IR, DSC, TGA and X-RPD, whose data are here included by reference.

According to a preferred embodiment of the process of the present invention, the process comprises the following steps a), b), c), obtaining the purified compound (IX) and the consecutive steps e), f), g), h), i) thus obtaining Apixaban of formula (I).

Indeed, performing both the steps from a) to c) and from e) to i), it is possible to achieve the lowest level of the impurities of formula (II) and/or (Ill) into Apixaban. In particular, said further decrease of the level of the dimer impurity of formula (II) and/or formula (III) is due to the combined used of the all steps of the process of the present invention. These results were obtained by means of the following process starting from the step a), proceeding in the step b), whit the filtration to remove the dimer impurity of formula (VI) and/or the dimer impurity of formula (VII) and finally obtaining a solution comprising the purified compound of formula (IX). The latest compound is converted to the compound of formula (VIII), which following the step e) and then f) is filtered to remove the dimer impurity of formula (IV) and/or the dimer impurity of formula (V), thus obtaining in the step g) a solution comprising the purified compound of formula (VIII), optionally can be carried out the step h), finally in the step i) the compound (VIII) is converted to Apixaban of formula (I), thus containing a low amount of dimer impurity of formula (II) and or dimer impurity of formula (III).

In particular, the process of the invention comprising the step a), b), c) and d), as already described, is preferred since it allows the earlier reduction of the dimer impurities, i.e. the amount of the dimer impurities is decreased in the first steps of the process for the preparation of Apixaban, thus avoiding the carry over of the dimer impurities through the synthesis and avoiding loss of more advanced intermediates which have an higher added value.

Moreover, said process comprising the steps a), b), c) and d) is preferred since is more efficient for reducing the dimer impurities, specifically the dimer impurity of formula (VI) and the dimer impurity of formula (VII), i.e. it provides the purification from the dimer impurities at higher extent.

During the development of the process of the present invention, it has been found the presence of some impurities, very difficult to be removed during the synthesis and that, at the end, contaminate the final pharmaceutical product Apixaban. In particular, already at the early stages of the synthesis, it has been observed the presence of impurities which contaminated the synthetic precursor intermediates of formula (IX) and (VIII), impurities having high relative retention times in the HPLC chromatograms.

Thus, another surprising aspect of the invention is the discovery of the presence of said impurities in Apixaban and precursors thereof and was also surprising, the nature, the structure and the origin of said impurities.

It has been indeed surprisingly found that during conversion of the compound of formula (XI) to the compound of formula (X):

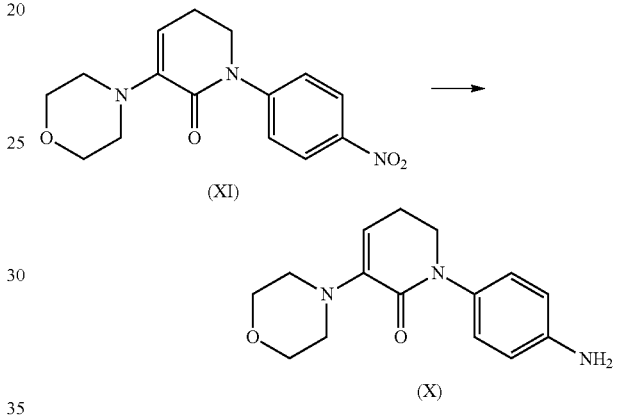

carried out by means of sodium sulfide, the dimer impurities of formula (VI) and (VII) are formed as by-product of said reaction:

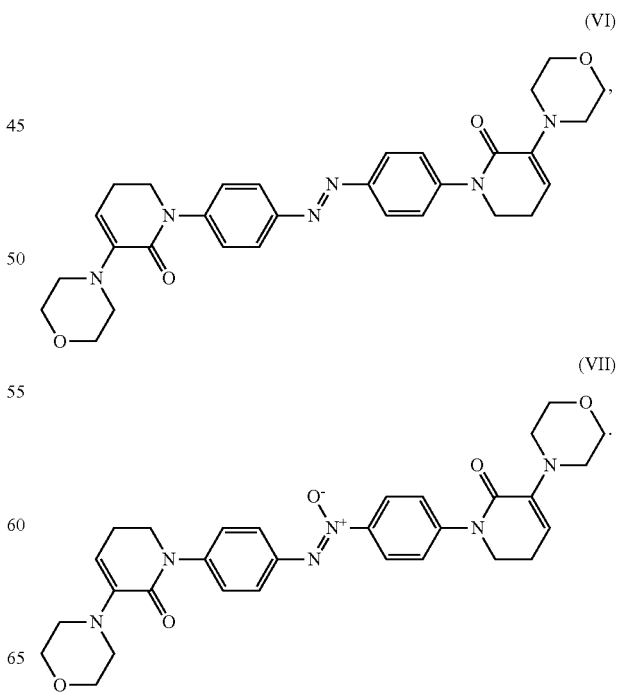

Moreover, it has been surprisingly found that said impurities proceed through the Apixaban synthesis undergoing to the same chemical transformations thus generating the dimer impurities of formula (IV) and (V) of the compound of formula (VIII) and, then, the dimer impurities of formula (II) and (III) of the compound Apixaban.

The FIG. 1 gives a picture of the origin and carry-over of the impurities through the Apixaban synthesis.

Furthermore considering said carry-over of the impurities, the process comprising the steps a), b), c) and d), as beforehand described, has the advantage of the reduction of dimer impurities, at the early stages of the synthesis, i.e. reduces the amount of the dimer impurity of formula (VI) and/or the dimer impurity of formula (VII) into the compound of formula (IX), thus providing the reduction of the correspondent related dimer impurities of the next intermediate and in Apixaban.

An aspect of the invention are thus the dimer impurities of Apixaban or a precursor thereof chosen in the group of:

A) (E)-6,6'-(4,4'-(diazene-1,2-diyl)bis(4,1-phenylene))bis(1-(4-methoxyphenyl)-7-oxo-4,5,6,7-tetrahydro-1H-pyrazolo[3,4-c]pyridine-3-carboxamide) having the following formula (II):

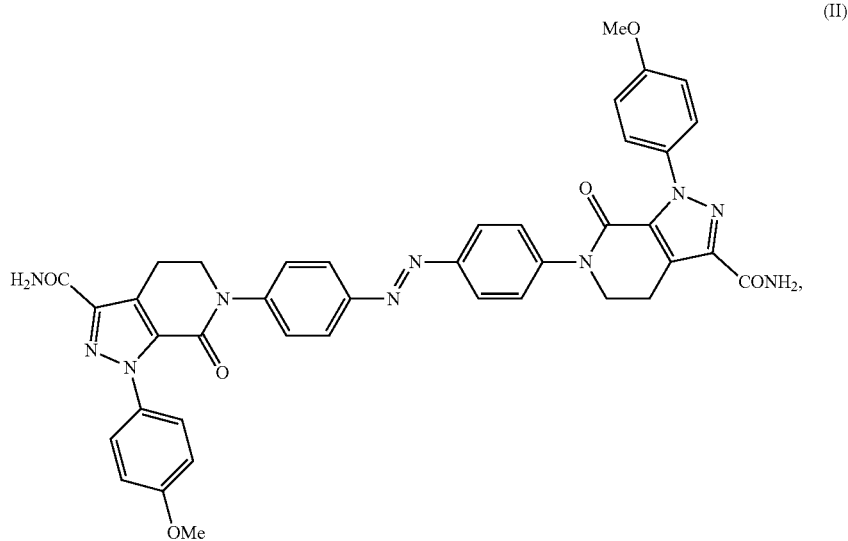

B) (Z)-1,2-bis(4-(3-carbamoyl-1-(4-methoxyphenyl)-7-oxo-4,5-dihydro-1H-pyrazolo[3,4-c]pyridin-6(7H)-yl)phenyl)diazene oxide having the following formula (III):

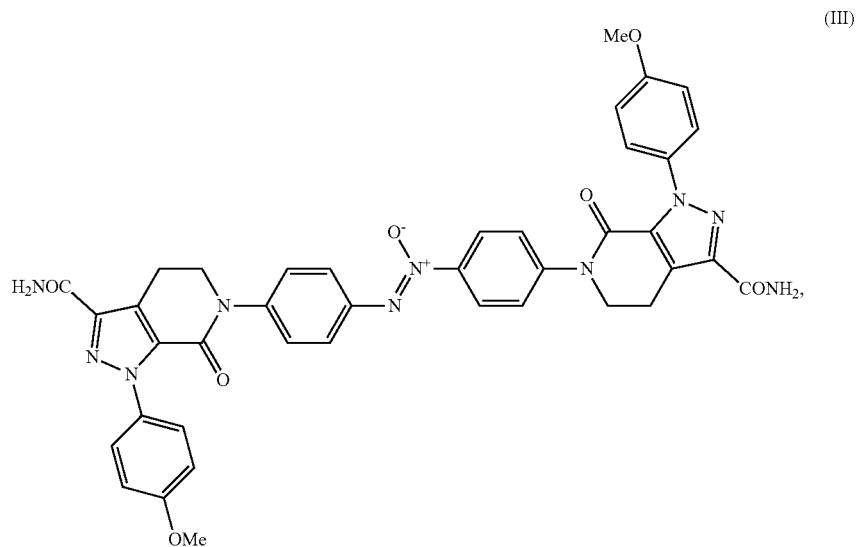 [SMILES: COc1ccc(-n2nc(C(N)=O)c3c2C(=O)N(c2ccc(/N=[N+](\[O-])c4ccc(N5CCc6c(C(N)=O)nn(-c7ccc(OC)cc7)c6C5=O)cc4)cc2)CC3)cc1]

C) (E)-1,1'-(4,4'-(diazene-1,2-diyl)bis(4,1-phenylene))bis(3-morpholino-5,6-dihydropyridin-2(1H)-one) having the following formula (VI):

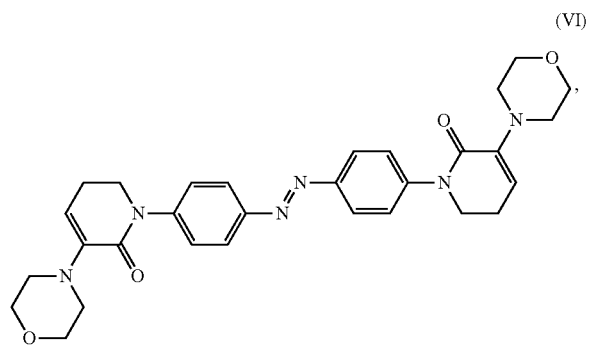 [SMILES: O=C1C(N2CCOCC2)=CCCN1c1ccc(/N=N/c2ccc(N3CCC=C(N4CCOCC4)C3=O)cc2)cc1]

D) (Z)-1,2-bis(4-(3-morpholino-2-oxo-5,6-dihydropyridin-1(2H)-yl)phenyl)diazene oxide having the following formula (VII):

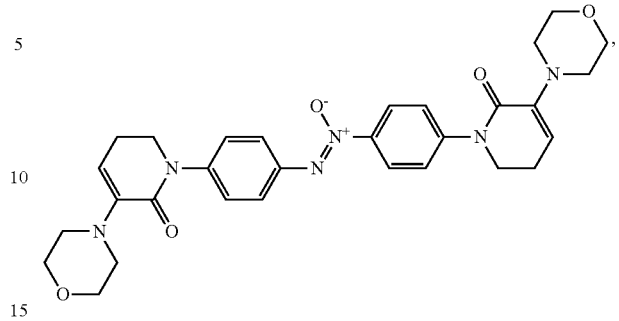

E) (E)-diethyl 6,6'-(4,4'-(diazene-1,2-diyl)bis(4,1-phenylene))bis(1-(4-methoxyphenyl)-7-oxo-4,5,6,7-tetrahydro-1H-pyrazolo[3,4-c]pyridine-3-carboxylate) having the following formula (IV):

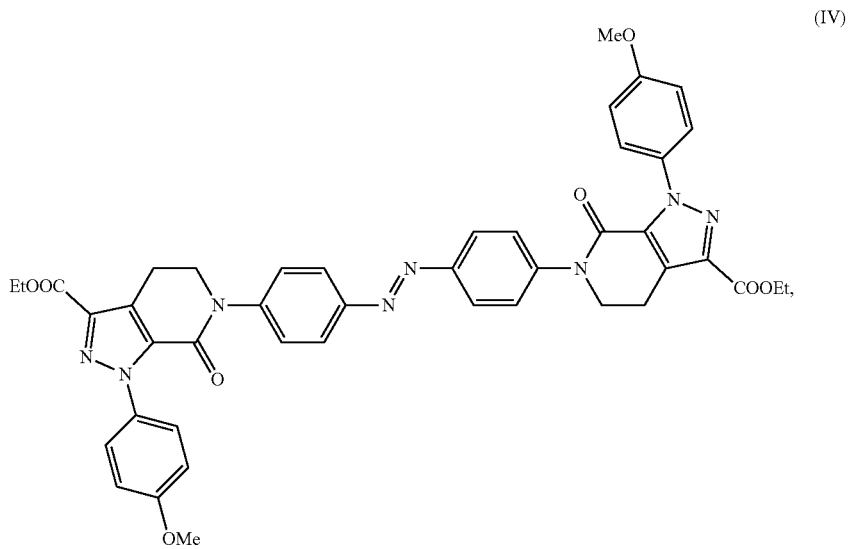 [SMILES: CCOC(=O)c1nn(-c2ccc(OC)cc2)c2c1CCN(c1ccc(/N=N/c3ccc(N4CCc5c(C(=O)OCC)nn(-c6ccc(OC)cc6)c5C4=O)cc3)cc1)C2=O]

F) (Z)-1,2-bis(4-(3-(ethoxycarbonyl)-1-(4-methoxyphenyl)-7-oxo-4,5-dihydro-1H-pyrazolo[3,4-c]pyridin-6(7H)-yl)phenyl)diazene oxide having the following formula (V):

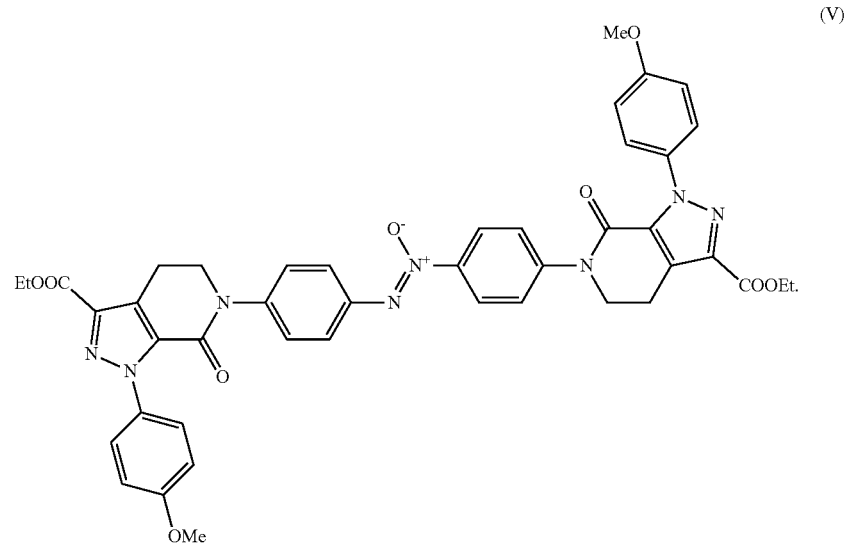 [SMILES: CCOC(=O)c1nn(-c2ccc(OC)cc2)c2c1CCN(c1ccc(/N=[N+](\[O-])c3ccc(N4CCc5c(C(=O)OCC)nn(-c6ccc(OC)cc6)c5C4=O)cc3)cc1)C2=O]

The dimer impurities of Apixaban or a precursor thereof above mentioned are yellow powders.

In particular, in FIGS. 3 and 4 are reported the UV-VIS spectra of the dimer impurities of Apixaban acquired by HPLC/DAD detector.

The dimer impurities are thus responsible from the colour of the Apixaban. In particular, said impurities confer to Apixaban a yellow colour. It is thus desirable that Apixaban does not contain said impurities to show a white colour.

As an other aspect it has been found that said dimer impurities of Apixaban and precursors thereof, and in particular the impurities of Apixaban of formula (II) and (III) are particularly insoluble in any solvent.

The (Z)-1,2-bis(4-(3-carbamoyl-1-(4-methoxyphenyl)-7-oxo-4,5-dihydro-1H-pyrazolo[3,4-c]pyridin-6(7H)-yl)phenyl)diazene oxide having the following formula (III):

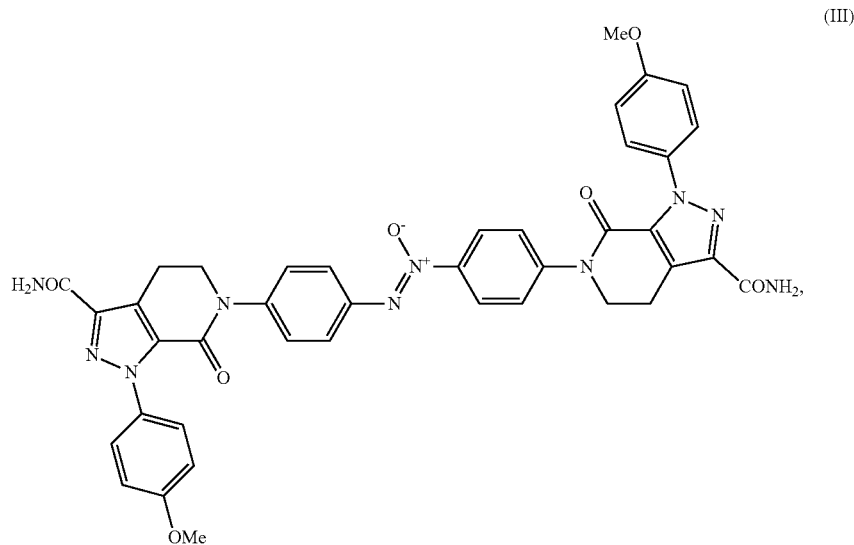 [SMILES: COc1ccc(-n2nc(C(N)=O)c3c2C(=O)N(c2ccc(/N=[N+](\[O-])c4ccc(N5CCc6c(C(N)=O)nn(-c7ccc(OC)cc7)c6C5=O)cc4)cc2)CC3)cc1]

(III)

it is a preferred dimer impurity of Apixaban of formula (I). Said impurity is a yellow powder.

In particular, said dimer impurity of formula (III) has a UV spectrum which shows the higher an absorption at 360-370 nm, as shown in FIG. 4. Thus, said dimer impurity is a substance that shows a bright yellow colour.

The product of a chemical reaction is rarely a single compound having purity sufficient to meet the regulatory standards. By-products due to secondary reactions of the reagents used in the reaction can also be present in the isolated product. In some steps of the production process of an active ingredient, such as Apixaban, the purity is analysed, generally by means of high performance liquid chromatography (HPLC), LC/MS, gas chromatography (GC) or thin layer chromatography (TLC), for defining if it is suitable for the subsequent treatment and lastly for use in the pharmaceutical product.

Generally, the impurities are identified spectroscopically, thus a chromatographic peak position, such as that of a chromatogram or a spot on a TLC panel, is associated thereto.

Once a peak position has been associated to a particular impurity, the impurity can be identified in a sample for the relative position thereof in the chromatogram, where the position in the chromatogram is measured in minutes between the injection of the sample in a column and elution of the impurity through the detector. The position in the chromatogram is known as the retention time and the ratio between the retention times is known as the relative retention time.

A man skilled in pharmaceutical art knows that a relatively pure compound may be used as a reference standard. A reference standard is similar to a reference marker, except for the fact that the first can be used not only for detecting the impurities, but also for quantifying the amount of impurities present in the sample of active ingredient.

As known to those skilled in the art, the management of process impurities is considerably improved by understanding the chemical structures thereof, the synthetic routes and identifying the parameters that affect the amount of impurities in the final product, for example by means of DOE.

The impurities of Apixaban, including the intermediates not entirely reacted, the impurities of the raw materials, the by-products of reaction, the degradation products, as well as other products, may affect the quality and efficiency of the pharmaceutical form containing Apixaban. Thus, there arises the need for a method for defining the level of impurities, with a special focus for the dimer impurities of Apixaban in samples of Apixaban, especially for bulk productions of the drug Apixaban.

It has been thus found a method for the determination in Apixaban of the dimer impurity of Apixaban having the following formula (II) and/or of formula (III):

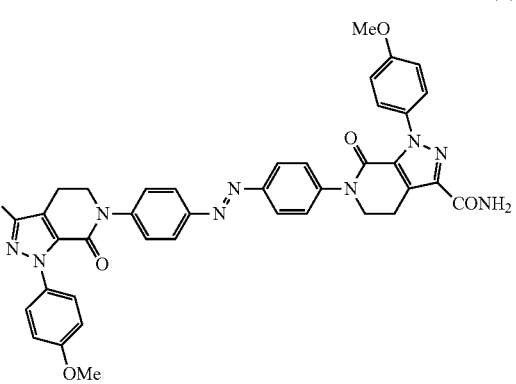

(II)

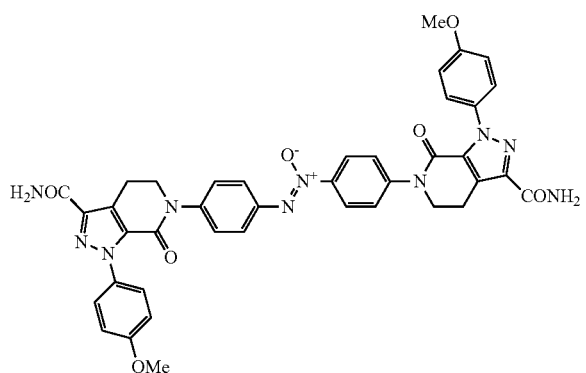

The dimer impurities of formula (II) and/or of formula (III) can be indeed used according to the following analytical methods the identification and/or quantification of said dimer impurities of formula (II) and of formula (III) in Apixaban.

A method for detecting or identifying the dimer impurity of formula (II) and/or of formula (III) in Apixaban comprises the following steps:

a) adding a known amount of dimer impurity of formula (II) and/or of formula (III) to the Apixaban sample, b) carrying out HPLC or LC/MS analysis of the Apixaban sample of step a), c) detecting the HPLC or LC/MS peak of the dimer impurity of formula (II) and/or of formula (III); or, a1) analyzing the dimer impurity of formula (II) and/or of formula (III) by means of HPLC or LC/MS, b1) analyzing the Apixaban sample by means of HPLC or LC/MS, c1) detecting the HPLC or LC/MS peak of the dimer impurity of formula (II) and/or formula (III) by comparing the retention times or relative retention times; or;

by means of LC/MS analysis detecting the peak having [M+1]$^+$ equal at 751 or 767 amu.

Besides the identification of the impurity peak in Apixaban, according to another aspect of the invention, it has been found a method for the quantification in Apixaban of the dimer impurities of Apixaban having the following formula (II) and/or formula (III):

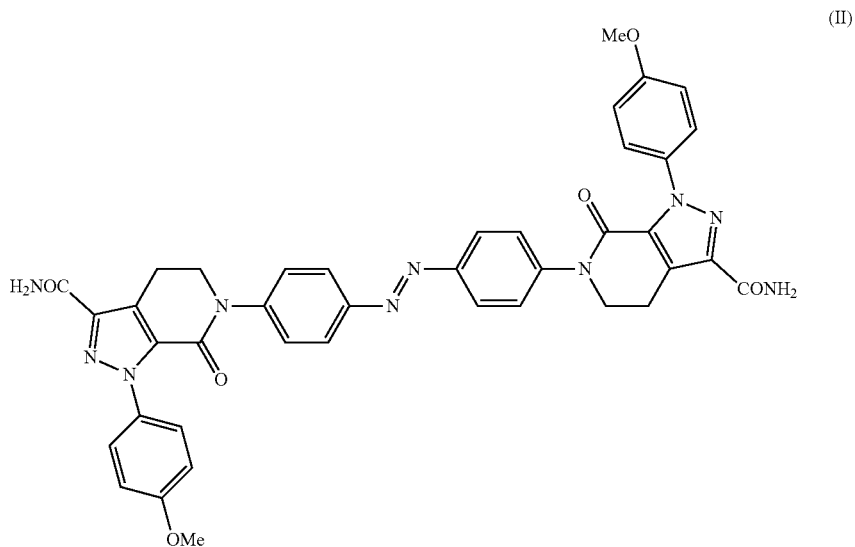

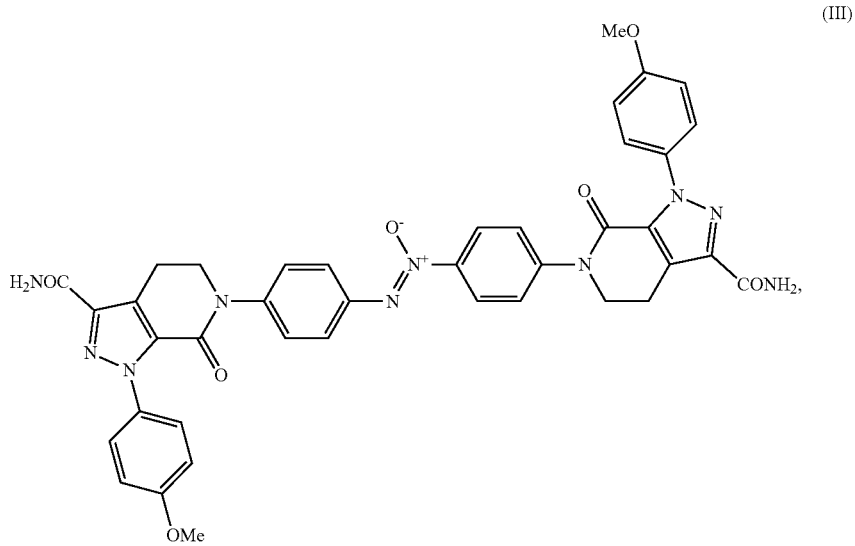 [SMILES: COc1ccc(-n2nc(C(N)=O)c3c2C(=O)N(c2ccc(/N=[N+](\[O-])c4ccc(N5CCc6c(C(N)=O)nn(-c7ccc(OC)cc7)c6C5=O)cc4)cc2)CC3)cc1]

comprising the following steps:

a) measuring the peak areas corresponding to each single dimer impurities of formula (II) and/or formula (III) in the Apixaban sample having an unknown amount of these compounds by means of HPLC or LC/MS, b) measuring the peak areas corresponding to a "reference standard" containing a known amount of dimer impurity of formula (II) and/or of formula (III) by means of HPLC or LC/MS, c) defining the amount of dimer impurities in Apixaban comparing the areas measured in the step a) with that measured in the step b).

According to a preferred embodiment of the process of the present invention, the method for the determination in Apixaban of the dimer impurity of Apixaban has the following formula (III):

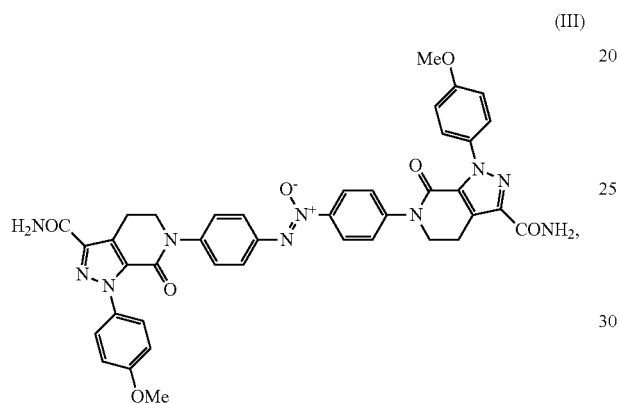
(III)

and the method for the quantification in Apixaban of the dimer impurity of formula (III) comprise everyone of the steps beforehand described, respectively from a) to c1) for the method for the determination in Apixaban of the dimer impurities and from a) to c) for the method for the quantification in Apixaban of the dimer impurity.

Another aspect of the invention is that the following dimer impurities of Apixaban:

a) dimer impurity of formula (II):

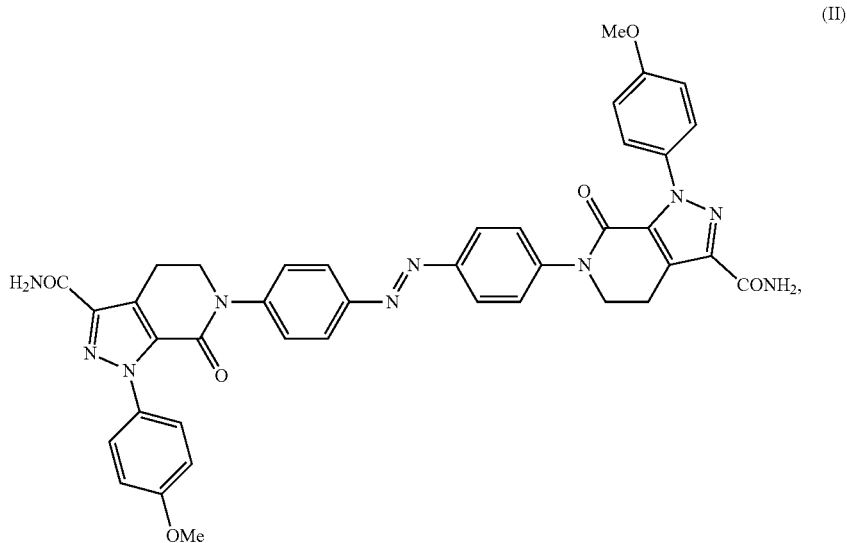
(II)

b) dimer impurity of formula (III):
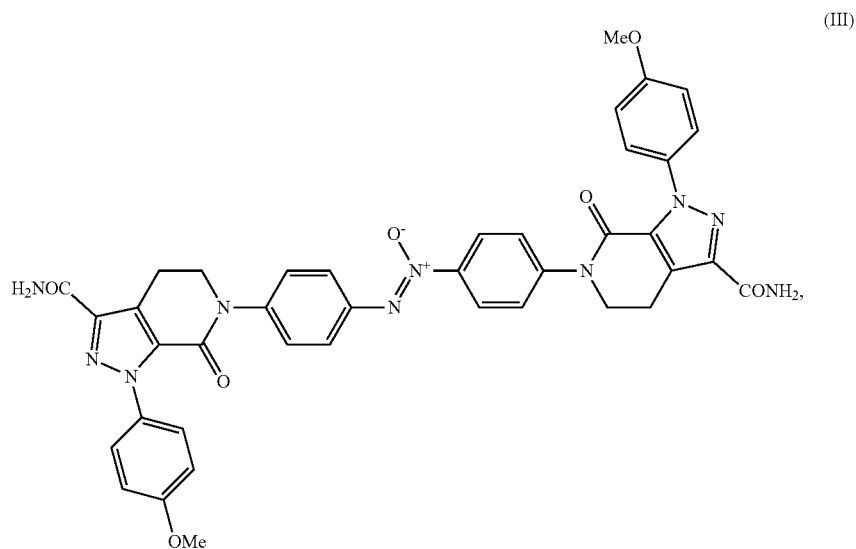
(III)
can be used as a "reference marker" or "reference standard" for the identification and/or the quantification of said dimer impurity in Apixaban of formula (I):
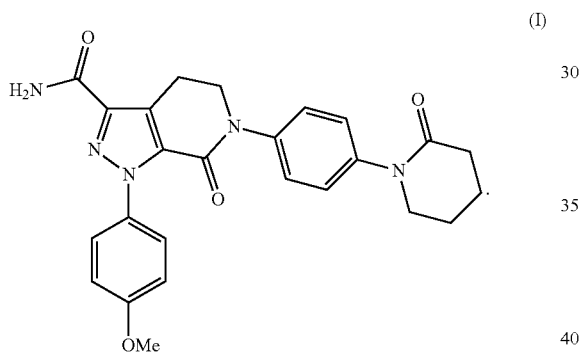
(I)
According to a preferred embodiment of the process of the present invention, the dimer impurity of Apixaban is the dimer impurity of formula (III):
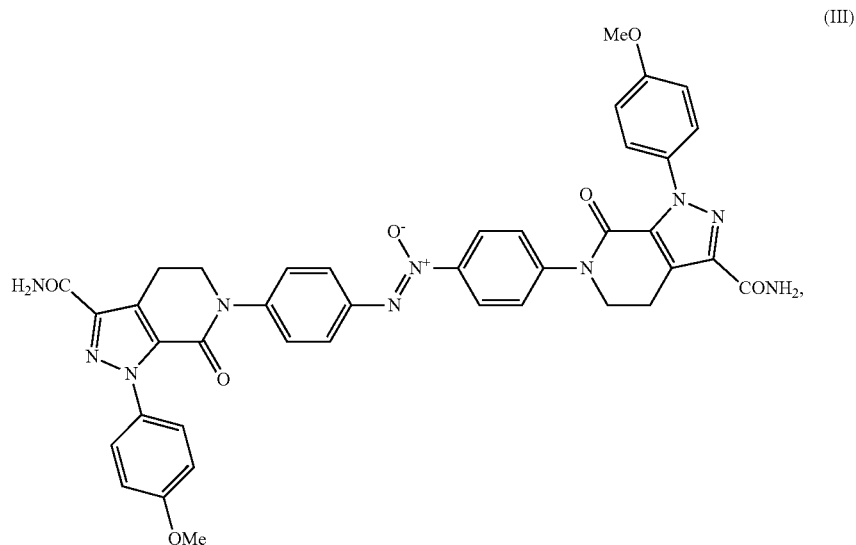 [SMILES: COc1ccc(-n2nc(C(N)=O)c3c2C(=O)N(c2ccc(/N=[N+](\[O-])c4ccc(N5CCc6c(C(N)=O)nn(-c7ccc(OC)cc7)c6C5=O)cc4)cc2)CC3)cc1]
(III)

which can be used as a "reference marker" or "reference standard" for the identification and/or the quantification of said dimer impurity in Apixaban of formula (I).

Also the following dimer impurities can be used as a "reference marker" or "reference standard" for the identification and/or the quantification of said dimer impurities in the relative following compounds:

c) Dimer impurity of formula (IV) and/or dimer impurity of formula (V):

(IV)

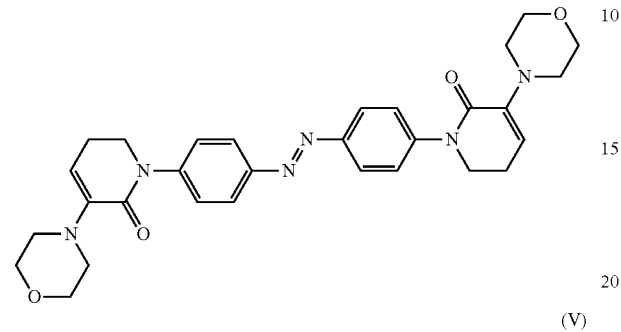

(V)

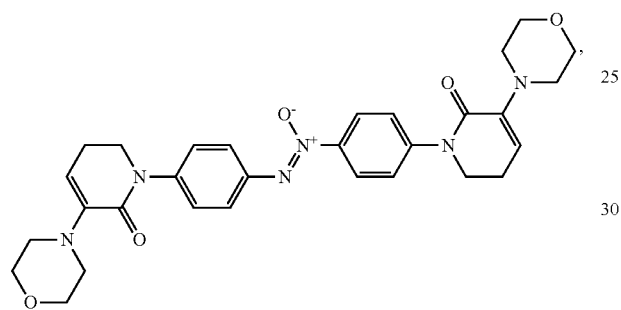

in compound of the following formula (X):

(X)

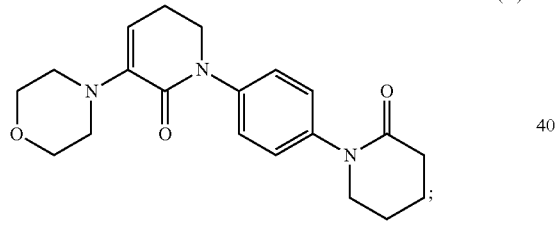

d) Dimer impurity of formula (VI) and/or dimer impurity of formula (VII):

(VI)

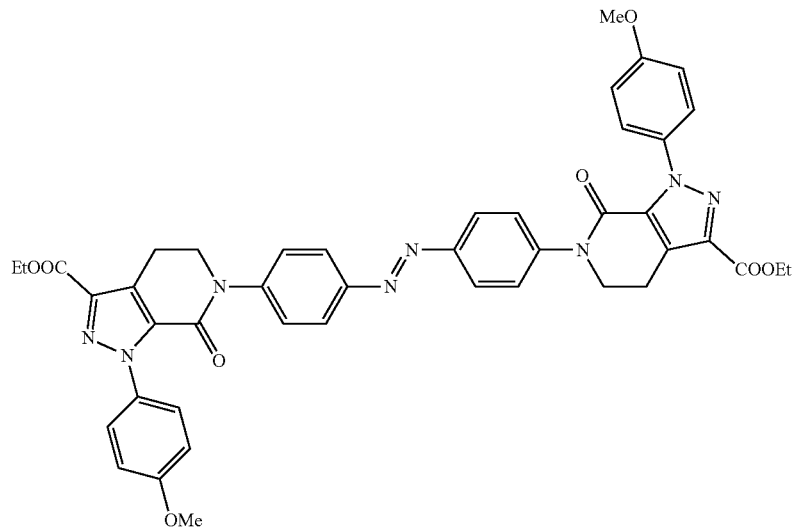

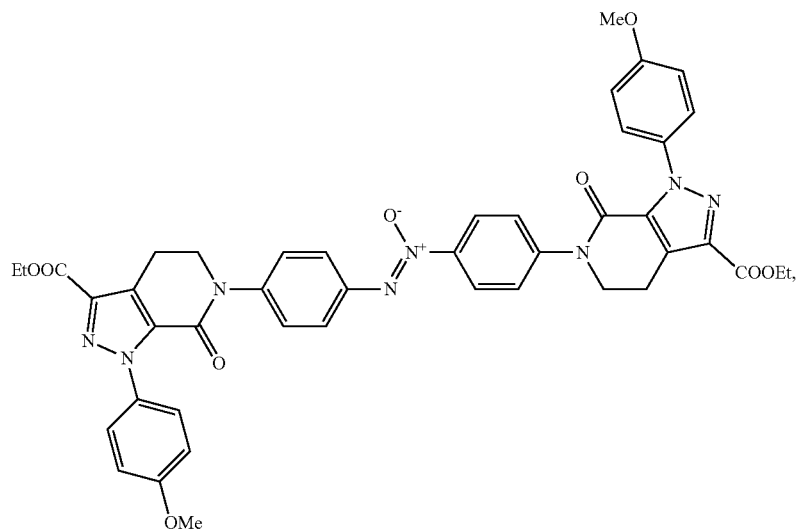
(VII)
in compound of the following formula (XI):
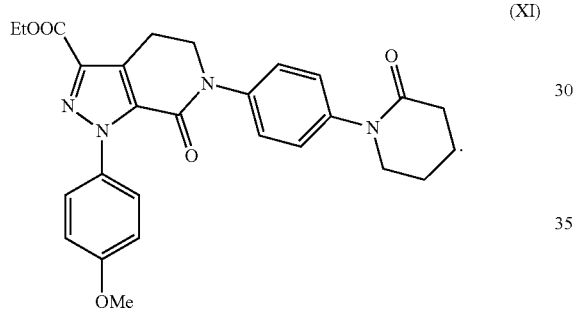
(XI)
According to a preferred embodiment of the process of the present invention, the method for the quantification into Apixaban of amounts comprised between 1 and 100 parts per millions of the dimer impurity of Apixaban having the following formula (II) and/or having formula (III):
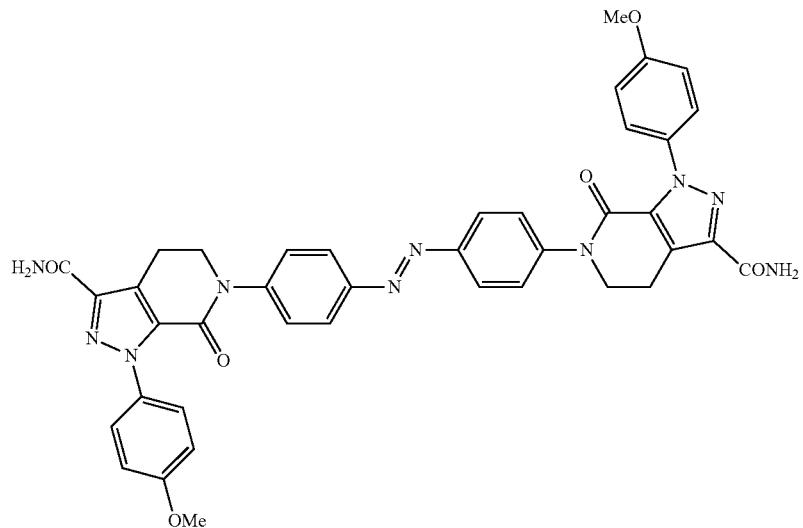
(II)

-continued
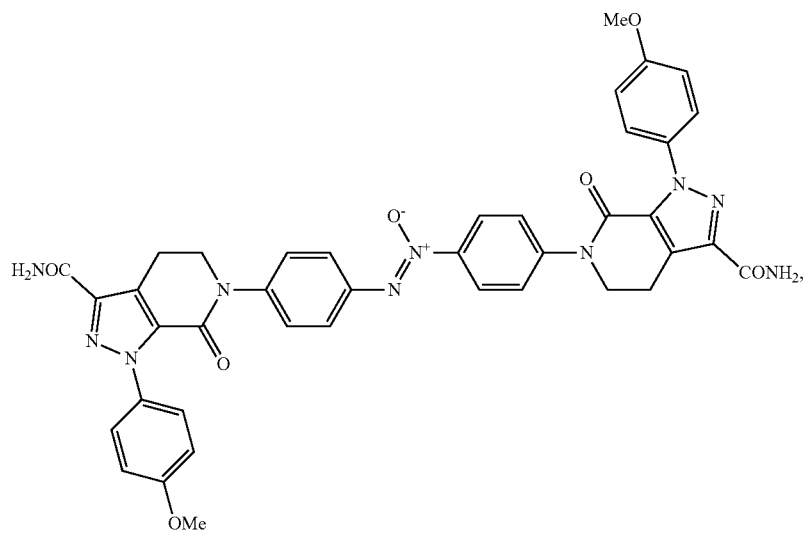
is carried out by LC/MS.
According to another aspect of the present invention, the dimer impurities of Apixaban of formula (II) and/or formula (III):
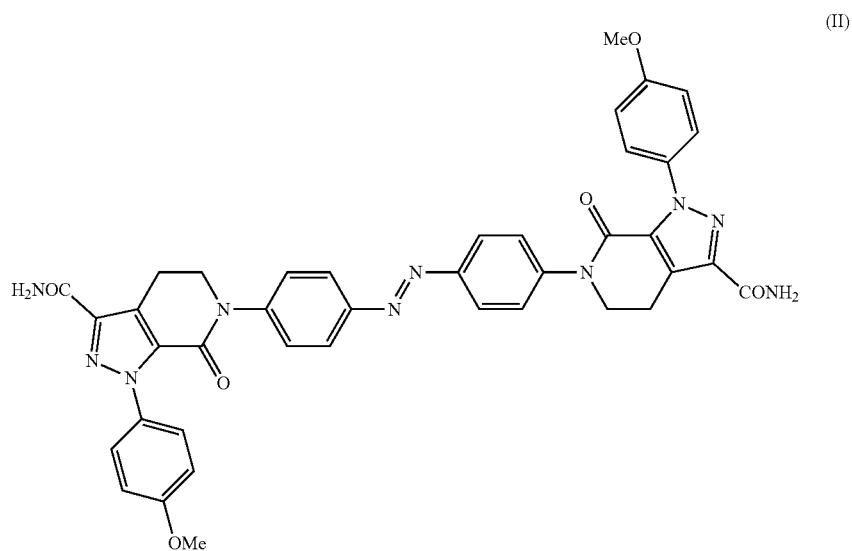

-continued (III)

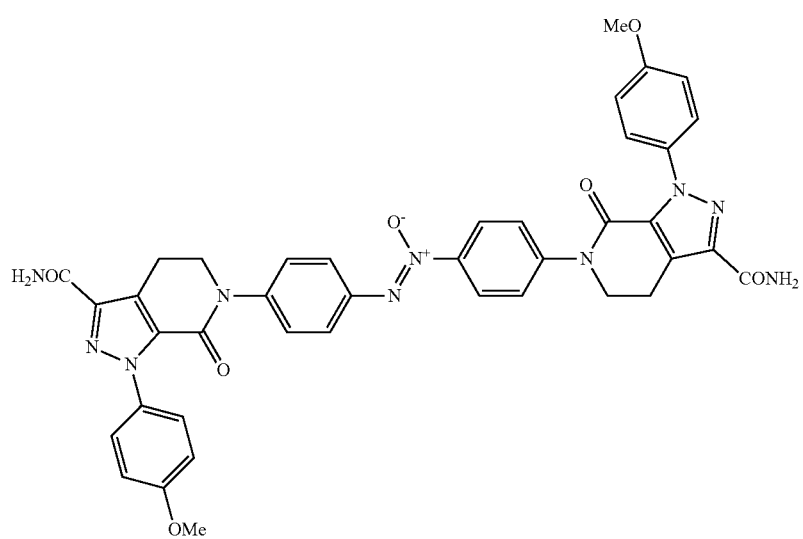

can be prepared according to a process comprising the following steps:

a) preparing a solution of 3-morpholino-1-(4-(2-oxopiperidin-1-yl)phenyl)-5,6-dihydropyridin-2(1H)-one of formula (IX):

(IX)

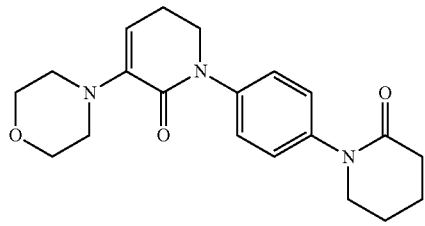

in a mixture of C1-C3 alcohol and water;

b) filtering the solution prepared in the step a), c) collect the solid on the filter comprising the following dimer impurities: a dimer impurity of formula (VI) and/or a dimer impurity of formula (VII):

(VI)

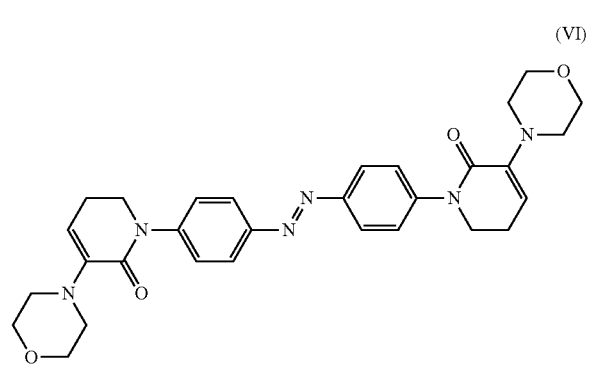

-continued (VII)

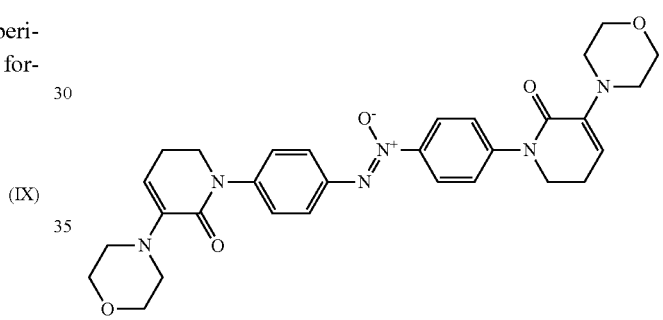

d) separating the dimer impurities of formula (VI) and (VII), e) conversion of the impurity of formula (VI) and/or formula (VII) of step d) to dimer impurity of Apixaban of formula (II) and/or (III).

Or, alternatively, the steps from a) to e) are substituted by the following steps:

f) preparing a solution of ethyl 1-(4-methoxyphenyl)-7-oxo-6-(4-(2-oxopiperidin-1-yl)phenyl)-4,5,6,7-tetrahydro-1H-pyrazolo[3,4-c]pyridine-3-carboxylate of formula (VIII):

(VIII)

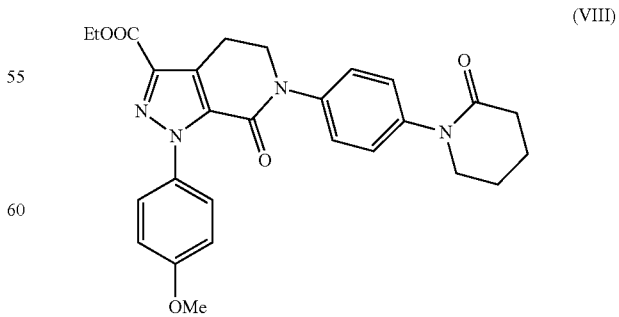

in a C1-C4 alcohol;

g) filtering the solution prepared in the step f), h) collect the solid on the filter comprising the following dimer impurities: a dimer impurity of formula (IV) and/or a dimer impurity of formula (V):

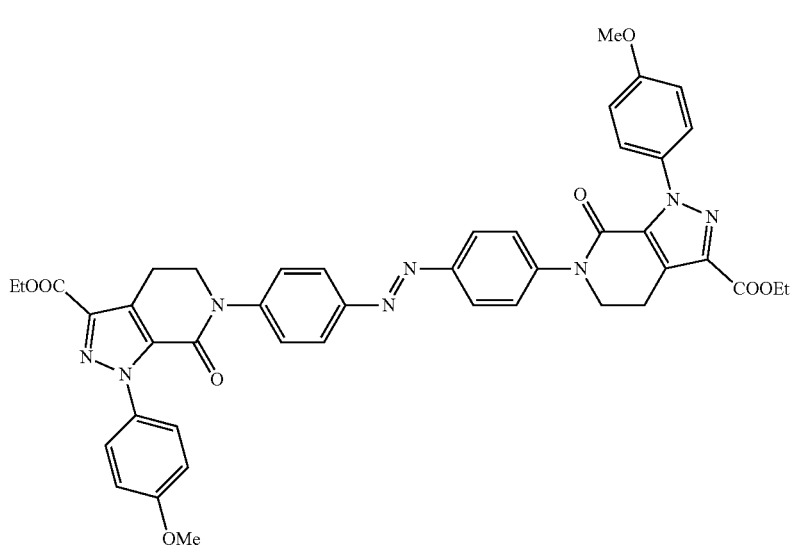

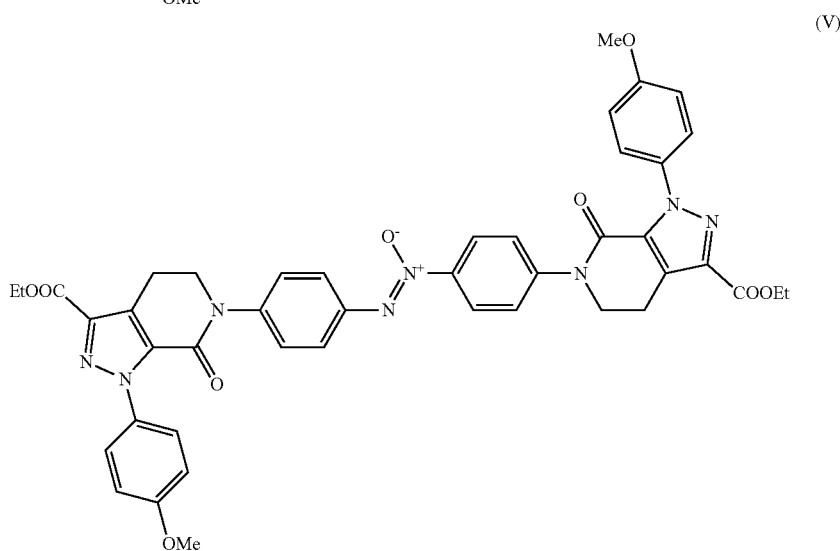

i) separating the dimer impurity of formula (IV) and/or (V),
j) conversion of the compound of formula (IV) and/or compound (V) of the step i) to dimer impurities of Apixaban of formula (II) and/or (III).

The separation steps d) and i) can be carried out by means of chromatographic separations such as for example by preparative HPLC, preparative TLC or by classic chromatographic column. In the latter case the classic chromatographic column can be conveniently filled with silica gel and the compounds are separated by elution with a mixture of Heptanes/AcOEt, preferably in gradient.

The step e) of conversion of the impurity of formula (VI) and/or formula (VII) of step d) to dimer impurity of Apixaban of formula (II) and/or (III) follows the same process, disclosed in prior art, to convert the compound of formula (IX) to compound of formula (VIII), having the distinct significant difference the replacement of the starting material, that is the compound (IX), with the impurity of formula (VI) and/or formula (VII). In particular, following this process it is afforded the impurity of formula (IV) and/or the impurity of formula (V). Later, the conversion of the last obtained impurity (IV) and/or (V) to the impurity of Apixaban of formula (II) and/or (III) is carried out following the same process, disclosed in prior art, to convert the compound of formula (VIII) to compound of formula (I), having the distinct significant difference the replacement of the starting material, that is the compound (VIII), with the impurity of formula (IV) and/or formula (V).

Methods of prior art for the preparation of Apixaban including the preparation of the compound of formula (X) by reduction with sodium sulphide such as those disclosed in Synthetic Communications, 43; 72-79, 2013, provide Apixaban containing impurities of formula (II) and (III) in amounts comprised between 0.28% and 1.0%.

Another aspect of the present invention is the Apixaban itself, since the process of the present invention allows the preparation of Apixaban containing from 0.00% to 0.10% of dimer impurity of formula (II) and/or of formula (III) as determined by HPLC A/A %; said amount is bounded to the starting amount of the first impurity of formula (VI) and/or (VII), that are generated during the preparation of the compound of formula (X) and brought to the compound of formula (IX), without changing the chemical structures and the relative amounts.

In particular, starting from an amount comprised between 5% and 2% of the dimer impurity of formula (VI) and/or formula (VII) present in the compound of formula (IX), following the process of the present invention, in particular the steps from a) to d), it is allowed the reduction or removal of the said dimer impurities to the amount comprised form 0.10% to 0.02% of the impurities of formula (II) and/or (III) in Apixaban, as determined by HPLC A/A %.

Figure 2:
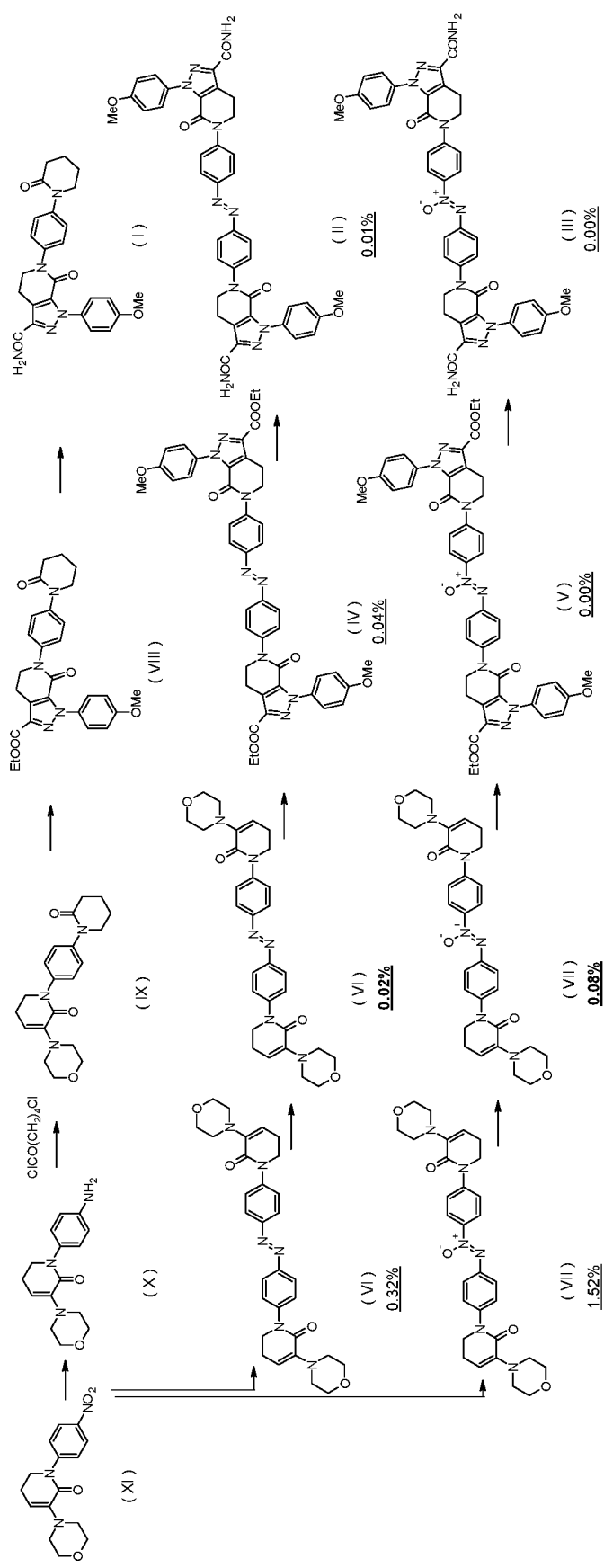
FIG. 2 shows an overall scheme of synthesis of Apixaban, according to the process of the present invention.

Instead, starting from an amount comprised between 2% and 0% of the dimer impurity of formula (VI) and/or formula (VII) present in the compound of formula (IX), following the process of the present invention, in particular the steps from a) to d), it is allowed the reduction or removal of the said dimer impurities to the amount comprised form 0.02% to 0.00% of the impurities of formula (II) and/or (III) in Apixaban, as determined by HPLC A/A % (see FIG. 2).

Therefore, another aspect of the present invention is the final product Apixaban having a very reduced amount of dimer impurity of formula (II) and/or of formula (III) as determined by HPLC A/A %.

In particular, thus, another aspect of the invention is Apixaban containing from 0.02% to 0.10% of dimer impurity of formula (II) and/or of formula (III), determined by HPLC A/A %, Apixaban as obtained by the process according to the present invention of the steps from a) to d), comprising the conversion to Apixaban of the compound of formula (IX) comprising, an amount comprised between 5% and 2%, as determined by HPLC A/A %, of the dimer impurities of formula (VI) and/or formula (VII).

According to another aspect, Apixaban containing from 0.02% to 0.10% of dimer impurity of formula (II) and/or of formula (III), determined by HPLC A/A %, is obtained by the process according to steps from e) to i) of the present invention, comprising the conversion to Apixaban of the compound of formula (VIII) comprising, an amount comprised between 2% and 5%, as determined by HPLC A/A %, of the dimer impurities of formula (IV) and/or formula (V). In such a case the option step h) of repeating the purification step have to be carried out one or more times.

FIG. 1 shows an overall scheme of synthesis of Apixaban, including the carry-over of the impurities through said synthesis in terms of chemical structures and amounts of said impurities, said amounts according to prior art methods.

By comparison of the FIG. 2 that shows an overall scheme of synthesis of Apixaban, including the process according to the present invention (steps from a) to d), it is clear the effect brought by the present invention since the amount of the impurities in the intermediate (IX) and then in the final Apixaban is well lower than in the prior processes (see FIG. 1).

As a note, the amount of impurity of formula (IV) and (V) through the process seems to increase especially during the conversion of the compound of formula (IX) to the compound (VIII). This is due to an increase aromaticity of the molecule (IV) and (V) compared to the molecule (VI) and (VII), therefore to an increased adsorption, i.e. to an increased response of the detector. Therefore such as an increase it is only apparent and not real in terms of actual amount of said impurities.

As a further aspect of the present invention, it should be considered that the dimer impurities of Apixaban comprise azo or azoxy functional group, thus being azo or azoxy compounds, hence there is high probability of a significant carcinogenic risk, according to the provisions of the "Guideline On The Limits Of Genotoxic Impurities" by EMEA, dated 2006 and line guide ICH M7 dated 23 Jun. 2014.

Indeed, azoxy compounds are a group of chemical compounds sharing a common functional group with general structure $RN=N^+(O^-)R$, said functional group is present in some of dimer impurities of Apixaban, i.e. the dimer impurity of formula (VII), the dimer impurity of formula (V) and the dimer impurity of formula (III).

Therefore, an alert related to the potential genotoxicity of said dimer impurities have to be raised.

EXPERIMENTAL PART

Compounds are named using the basic rules of IUPAC Nomenclature.

Proton Magnetic Resonance (NMR) spectra were recorded either on Varian instruments at 400, MHz, or on a Bruker instrument at 300 MHz and 400 MHz. Chemical shifts are reported in ppm (δ) using the residual solvent line as internal standard. Splitting patterns are designed as s, singlet; d, doublet; t, triplet; q, quartet; m, multiplet; b, broad. The NMR spectra were recorded at a temperature ranging from 20° C. to 30° C.

Ultraviolet-visible (UV-Vis) was acquired by HPLC/DAD detector.

The following table lists the abbreviations used:

T Temperature

Eq. Equivalent

TEA Triethylaimine

THF Tetrahydrofuran

NMR Nuclear magnetic resonance

HPLC High performance liquid chromatography.

LC-MS Liquid chromatography-mass spectrometry

UV-Vis Ultraviolet-visible

DAD Diode-array detector

Example 1: Preparation of the Compound of Formula (IX) Comprising the Related Dimer Impurities: (E)-1,1'-(4,4'-(diazene-1,2-diyl)bis(4,1-phenylene))bis(3-morpholino-5,6-dihydropyridin-2(1H)-one) of Formula (VI) and (Z)-1,2-bis(4-(3-morpholino-2-oxo-5,6-dihydropyridin-1(2H)-yl)phenyl)diazene oxide of Formula (VII)

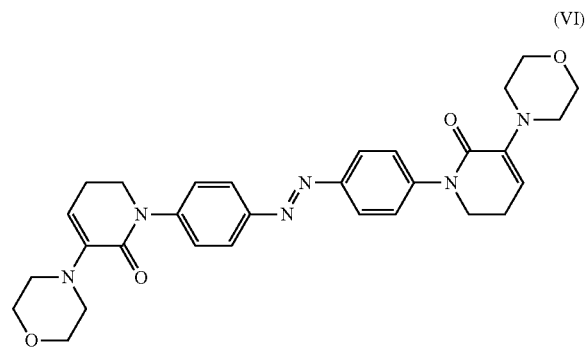

(VI)

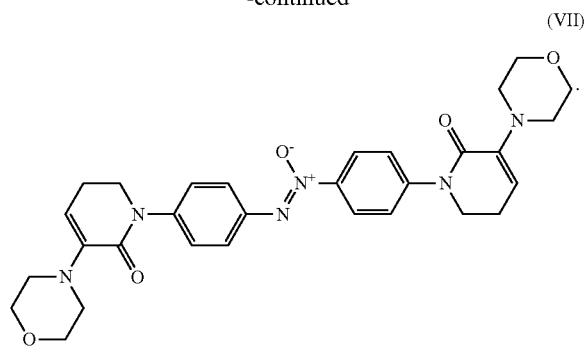

(VII)

Comparative Example

Synthesis Scheme:

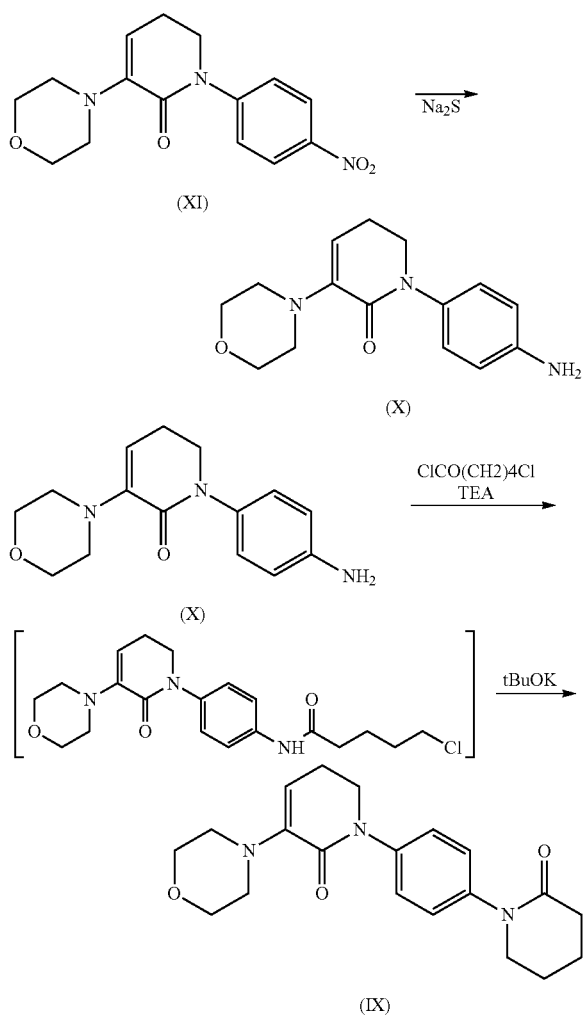

The compound of formula (X) could be prepared according to the method disclosed in the Journal Synthetic Communication, 2013, vol. 43, pag. 72-79, in particular, according to the paragraph entitled "1-(4-Aminophenyl)-3-(morpholin-4-yl)-5,6-dihydropyridin-2(1H)-one (13)" at pag. 76, starting from the compound of formula (XI).

Therefore, the compound of formula (X) was prepared according to the following method.

A solution of Sodium sulfate nonahydrate (197 g, 2.5 eq.) in water (350 mL) was dosed over 20 minutes at T=40/45° C. into a mixture of the compound of formula (XI) (100 g, 1.0 eq.) and methanol (1000 mL). The mixture was stirred at T=40/45° C. for additional 2 hours to reach reaction completion. The mixture was then distilled at reduced pressure and $T_{max}$=45° C. until 900 mL of solvent were removed. The resulting slurry was cooled down to T=20/25° C., kept stirring for 2 hours at this temperature and then filtered washing the wet cake with water (2×100 mL). Upon drying at reduced pressure and T=65° C. for 10 hours, 83 g of the compound of formula (X) were obtained. (92% yield, HPLC A %: the compound of formula (X) 96.09%).

Said compound of formula (X) thus obtained contained the following dimer impurities:

0.48% (HPLC A/A %) dimer impurity of formula (VI),
1.39% (HPLC A/A %) dimer impurity of formula (VII).

A 4-neck round bottom flask was charged with 60 g of said compound of formula (X) (1.0 eq.) (prepared as said above and containing the impurities of formula (VI) and (VII)), then with 51.1 g of triethylamine (TEA) (2.3 equiv.) and 600 mL of tetrahydrofuran (THF). A solution of 51 g of chlorovaleryl chloride (1.5 equiv.) in 120 mL of THF was dosed within 1-2 hours at T=0/5° C. The mixture is stirred at T=0/5° C. for additional 30 minutes, thereafter maintaining the same temperature, a solution of 73.9 g of potassium tert-butoxide (3.0 eq.) in 300 mL of THF is dosed over 30-45 minutes. After 30 minutes stirring at T=0/5° C., the mixture is warmed to T=20/25° C. for additional 2 hours. Once checked for reaction completion, the batch is distilled at reduced pressure and $T_{max}$=35° C. to residual 4 volumes (240 mL). The resulting slurry is diluted with 480 ml of water and distilled again under the same conditions to residual 9 volumes (900 mL). The mixture is stirred for at least 2 hours at T=20/25° C. and then filtered washing the wet cake with water (2×60 mL).

Upon drying at reduced pressure and T=65° C. for at least 8 hours, 64 g of the compound of formula (IX) are obtained (molar yield 82%). This solid contains the following dimer impurities:

0.17% (HPLC A/A %) dimer impurity of formula (VI),
1.9% (HPLC A/A %) dimer impurity of formula (VII).

Example 2: Preparation of the Following Compound of Formula (IX), Exemplificative of the Invention Synthesis Scheme:

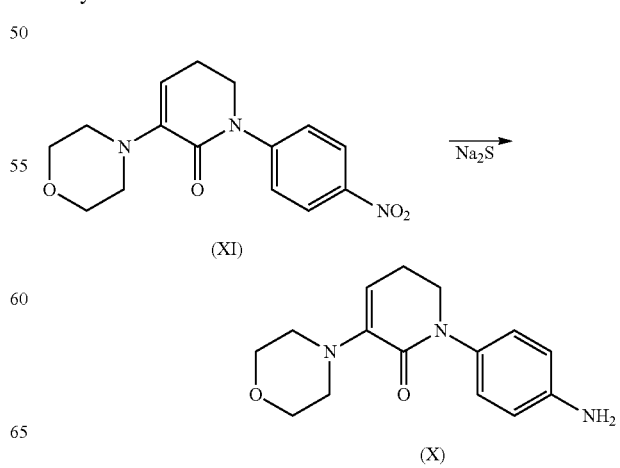

-continued

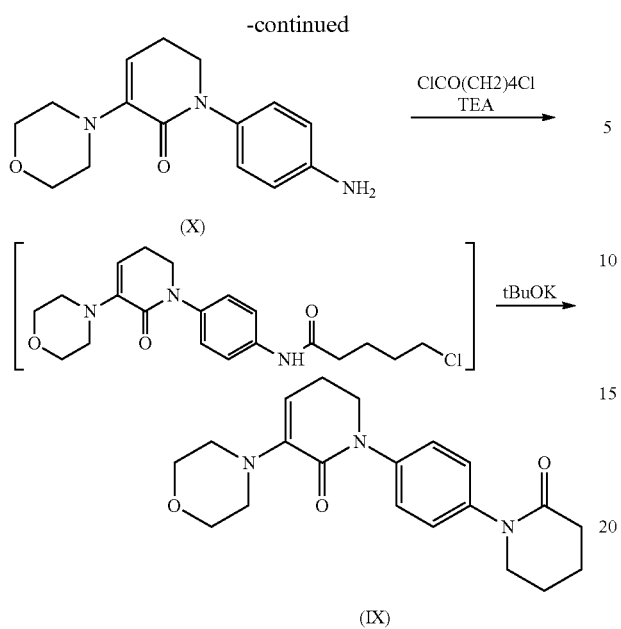

The compound of formula (X) could be prepared according to the method disclosed in the Journal Synthetic Communication, 2013, vol. 43, pag. 72-79, in particular, the paragraph entitled "1-(4-Aminophenyl)-3-(morpholin-4-yl)-5,6-dihydropyridin-2(1H)-one (13)" at pag. 76, starting from the compound of formula (XI).

Therefore, the compound of formula (X) was prepared according to the following method.

A solution of Sodium sulfate nonahydrate (197 g, 2.5 eq) in water (350 mL) was dosed over 45 minutes at T=40/45° C. into a mixture of compound of formula (XI) (100 g, 1.0 eq.) and methanol (1000 mL). The mixture was stirred at T=40/45° C. for additional 2 hours to reach reaction completion. The mixture was then distilled at reduced pressure and $T_{max}$=45° C. until 930 mL of solvent were removed. The resulting slurry was cooled down to T=20/25° C., kept stirring for 1 hour at this temperature and then filtered washing the wet cake with water (2×100 mL). Upon drying at reduced pressure and T=65° C. for 10 hours, 82 g of the compound of formula (X) were obtained. (91% yield, HPLC A %: compound of formula (X) 96.16%, Said compound of formula (X) thus obtained contained the following dimer impurities:

0.66% (HPLC A/A %) dimer impurity of formula (VI),
1.50% (HPLC A/A %) dimer impurity of formula (VII).

A 4-neck round bottom flask was charged with 80 g of said compound of formula (X) (1.0 eq.) (prepared as said above and containing the impurities of formula (VI) and (VII)), then with 68.3 g of triethylamine (TEA) (2.3 equiv.) and 800 mL of tetrahydrofuran (THF). A solution of 68.3 g of chlorovaleryl chloride (1.5 equiv.) in 160 mL of THF was dosed within 1-2 hours at T=0/5° C.

The mixture is stirred at T=0/5° C. for additional 30 minutes, thereafter maintaining the same temperature, a solution of 98.1 g of potassium tert-butoxide (3.0 eq.) in 400 mL of THF is dosed over 30-45 minutes. After 30 minutes stirring at T=0/5° C., the mixture is warmed to T=20/25° C. for additional 2 hours. Once checked for reaction completion, the batch is distilled at reduced pressure and $T_{max}$=35° C. to residual 6 volumes (480 mL) and then stripped with 560 mL of ethanol under the same conditions, again to residual 6 volumes (480 mL). The resulting mixture is diluted with 720 mL of ethanol and 880 mL of water, then the opalescent solution obtained is heated to T=40/45° C. and filtered on dicalite, washing with 80 mL of pre-heated ethanol (this solid cake is the starting material of the example 3). The filtered solution is distilled under reduced pressure to residual 6 volumes (480 mL). The mixture is cooled down to T=20/25° C. and stirred at this temperature for at least 1 hour. The slurry is finally filtered washing the wet cake with water (2×80 mL). Upon drying at reduced pressure and T=65° C. for at least 8 hours, 90.3 g of the compound of formula (IX) are obtained. (molar yield 86.8%).

This solid contained the following dimer impurities:
0.04% (HPLC A/A %) dimer impurity of formula (VI),
0.09% (HPLC A/A %) dimer impurity of formula (VII).

Example 3: Preparation of the Following Dimer Impurities of Formula (VI) and of Formula (VII)

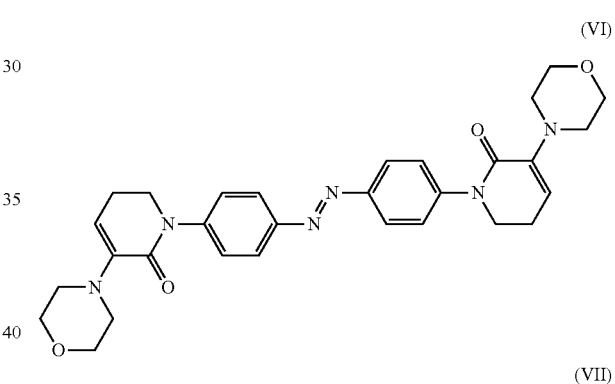

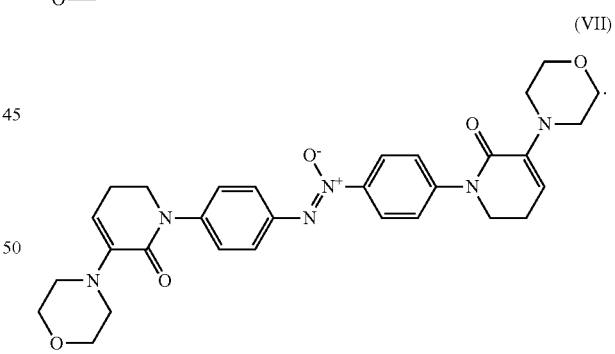

The insoluble substance in ethanolic solution collected (the solid cake of example 2 comprising dicalite and the dimer impurities of formula (VI) and (VII)) is charged into a round bottom flask equipped with a Dean-Stark apparatus and suspended in 600 mL of toluene. The mixture is heated to reflux removing water until the solvent boiling point is reached. The mixture is cooled down to T=80/90° C. and filtered. The solid collected, including the dimer impurities of formula (VI) and formula (VII) and dicalite, is charged into a round bottom flask and 500 mL of dichloromethane is added. The mixture is heated to reflux and filtered washing with dichloromethane (4×100 mL). The solution is then concentrated to residue under reduced pressure and the residue is taken up with acetone in order to obtain a stirrable slurry. The suspension is filtered affording 5.8 g of yellow solid which, upon HPLC analysis (FIG. 2), resulted as a mixture of the following two species:

16.9% (HPLC A/A %) of dimer impurity of formula (VI),
80.5% (HPLC A/A %) of dimer impurity of formula (VII).

The mixture was analysed also via NMR; since the two impurities differ only for the oxidation state of the diazo group their 1H chemical shifts are overlapping and the resulting spectrum appears as that of one single species. $^1$H-NMR (400 MHz, CDCl$_3$, ppm), d: 8.32 (dd, J1=8 Hz, J2=24 Hz 4H), 7.53 (m, 4H), 5.76 (bs, 2H), 3.88 (m, 12H), 2.96 (m, 8H), 2.57 (m, 4H). The aromatic carbons on the $^{13}$C-NMR and DEPT $^{135}$NMR spectra show a partial desymmetrisation while the aliphatic and the carbonyl groups show the same chemical shifts for the two species (100 MHz, CDCl$_3$, ppm), d: 161.4 (C), 145.7 (C), 145.1 (C), 143.8 (C), 143.7 (C), 143.6 (C), 141.3 (C), 126.3 (CH), 125.1 (CH), 124.6 (CH), 124.5 (CH), 123.3 (C), 122.8 (CH), 115.1 (CH), 114.7 (CH), 66.8 (CH$_2$), 50.6 (CH$_2$), 48.5 (CH$_2$), 23.4 (CH$_2$). HPLC-MS: 11.3 min ESI-MS m/z=559 (Dimer impurity of formula (VII) MW 558 [M+H]+), 11.9 min ESI-MS m/z=543 (Dimer impurity of formula (VI) MW 542 [M+H]+).

Example 4: Preparation of the Compound of Formula (I), Starting from the Compound of Formula (IX) of Example 2. Effect of the Invention on Apixaban Synthesis Scheme:

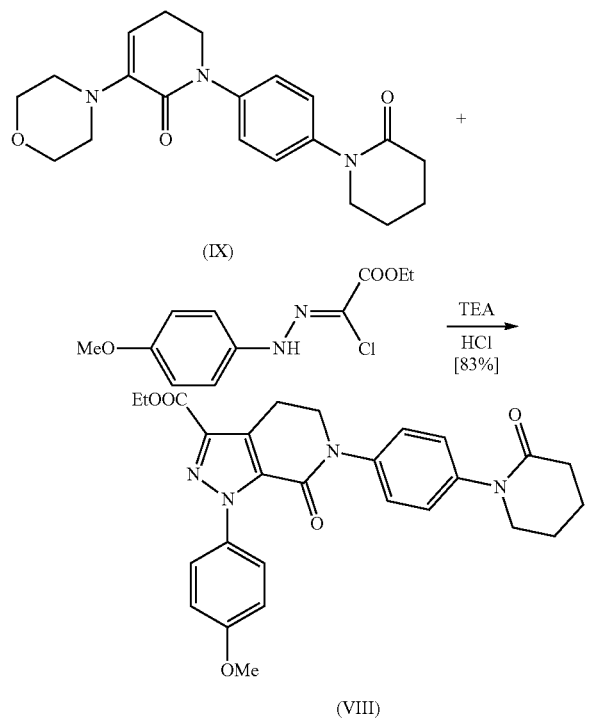

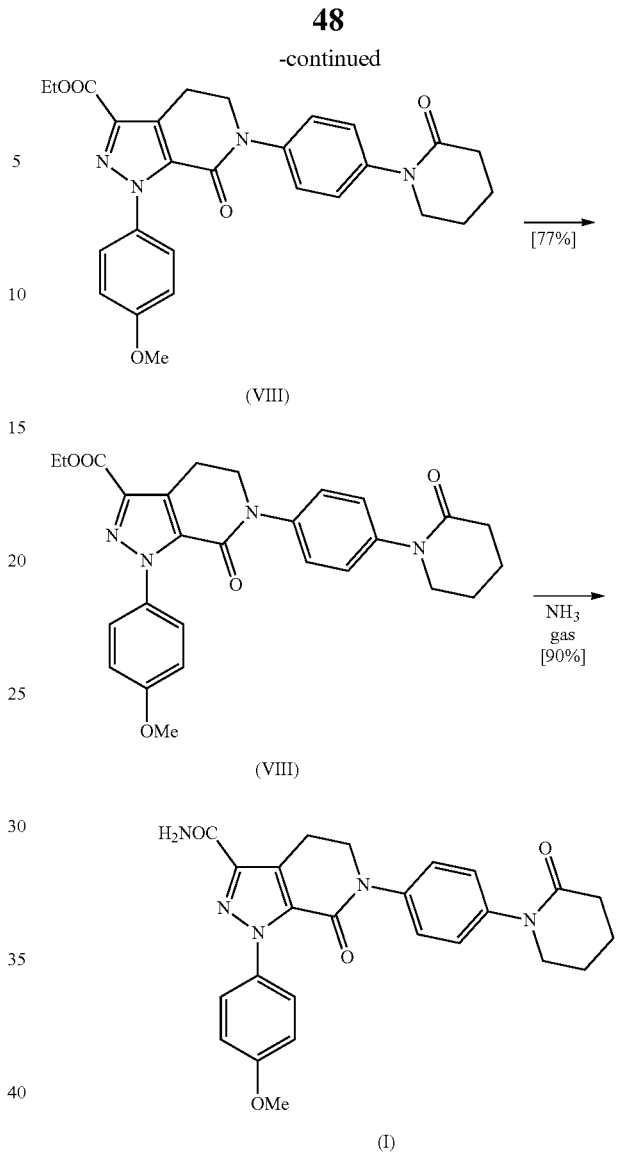

The compound of formula (VIII) was prepared according to the method disclosed in the Journal Synthetic Communication, 2013, vol. 43, pag. 72-79, in particular, the paragraph entitled "Ethyl 1-(4-methoxyphenyl)-7-oxo-6-(4-(2-oxopiperidin-1-yl)phenyl)-4,5,6,7-tetrahydro-1H-pyrazolo [3,4-c]pyridine-3-carboxylate (2)" at pag. 78, starting from the compound of formula (IX) prepared according to the example 2.

Later, performing the preparation according to the method described in Example 11 of EP Application EP14189007.9 or Example 6 of WO2007/001385, it was obtained the compound of formula (I), Apixaban, comprising of following dimer impurities of Apixaban:

0.00% of (E)-6,6'-(4,4'-(diazene-1,2-diyl)bis(4,1-phenylene))bis(1-(4-methoxyphenyl)-7-oxo-4,5,6,7-tetra hydro-1H-pyrazolo[3,4-c]pyridine-3-carboxamide) having the following structure (II):

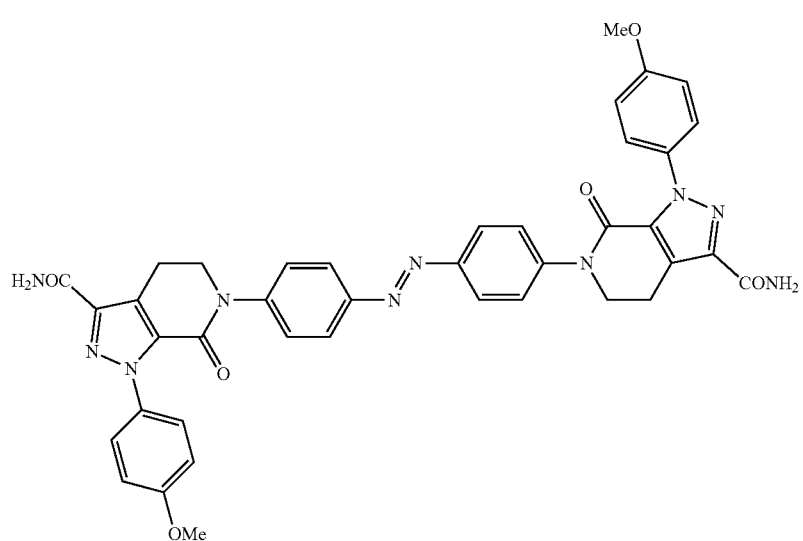
0.01% of (Z)-1,2-bis(4-(3-carbamoyl-1-(4-methoxyphenyl)-7-oxo-4,5-dihydro-1H-pyrazolo[3,4-c]pyridin-6(7H)-yl)phenyl)diazene oxide having the following structure (III):
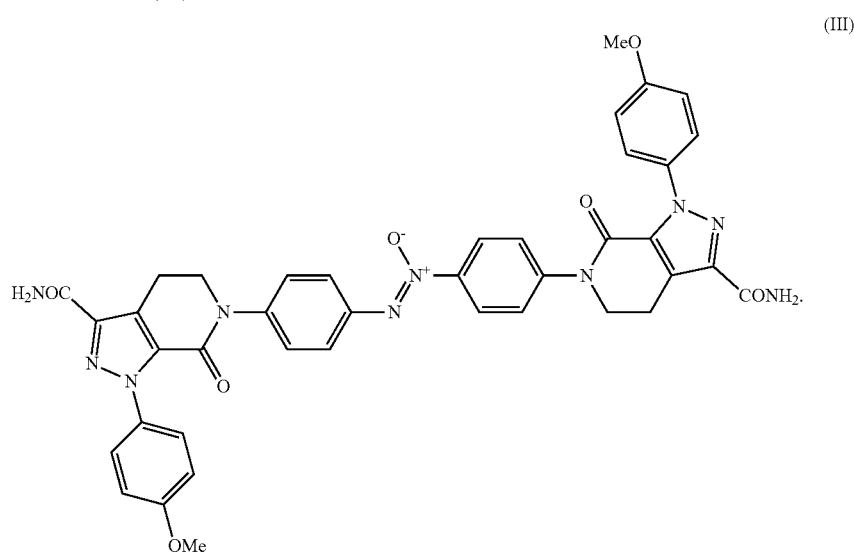
Example 5: Preparation of the Compound of Formula (VIII), Starting from the Compound of Formula (IX) of Example 1. Comparative Example
Synthesis Scheme:
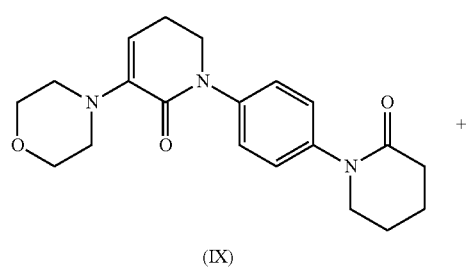
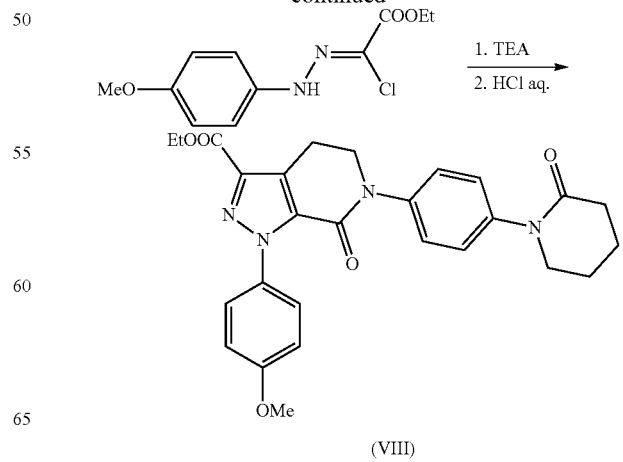

The compound of formula (VIII) was prepared according to the method disclosed in the Journal Synthetic Communication, 2013, vol. 43, pag. 72-79, in particular, the paragraph entitled "Ethyl 1-(4-methoxyphenyl)-7-oxo-6-(4-(2-oxopiperidin-1-yl)phenyl)-4,5,6,7-tetrahydro-1H-pyrazolo[3,4-c]pyridine-3-carboxylate (2)" at pag. 78, starting from the compound of formula (IX) prepared according to the example 1.

The obtained compound of formula (VIII) contained the following dimer impurities:

0.59% of (E)-diethyl 6,6'-(4,4'-(diazene-1,2-diyl)bis(4,1-phenylene))bis(1-(4-methoxyphenyl)-7-oxo-4,5,6,7-tetrahydro-1H-pyrazolo[3,4-c]pyridine-3-carboxylate) having the following structure (IV):

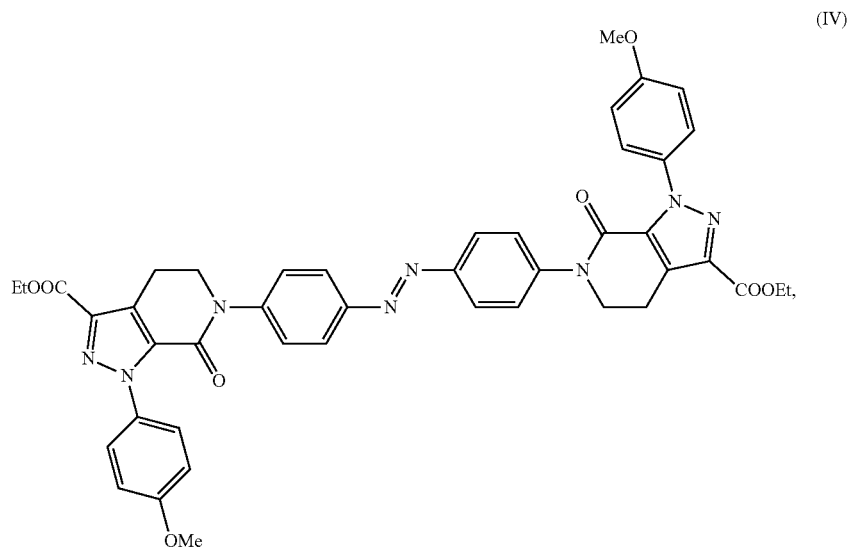 [SMILES: CCOC(=O)c1nn(-c2ccc(OC)cc2)c2c1CCN(c1ccc(/N=N/c3ccc(N4CCc5c(C(=O)OCC)nn(-c6ccc(OC)cc6)c5C4=O)cc3)cc1)C2=O]

1.61% of (Z)-1,2-bis(4-(3-(ethoxycarbonyl)-1-(4-methoxyphenyl)-7-oxo-4,5-dihydro-1H-pyrazolo[3,4-c]pyridin-6(7H)-yl)phenyl)diazene oxide having the following structure (V):

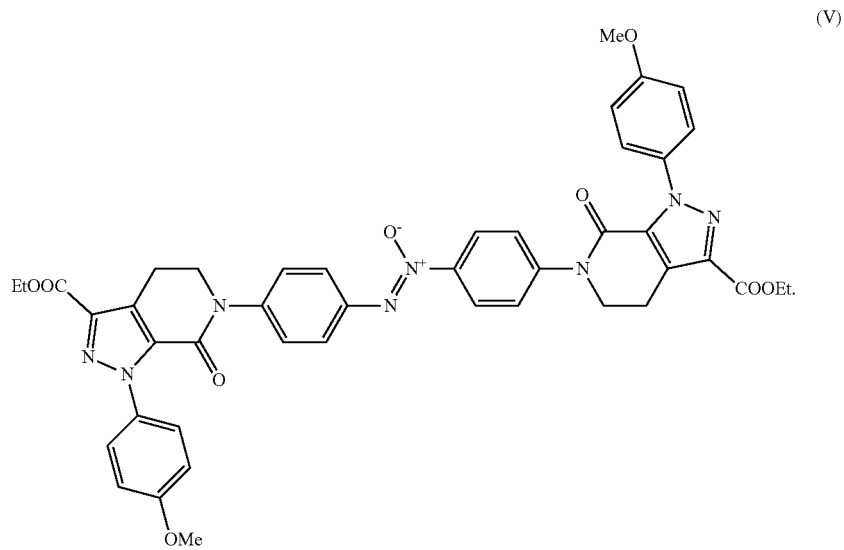 [SMILES: CCOC(=O)c1nn(-c2ccc(OC)cc2)c2c1CCN(c1ccc(/N=[N+](\[O-])c3ccc(N4CCc5c(C(=O)OCC)nn(-c6ccc(OC)cc6)c5C4=O)cc3)cc1)C2=O]

Example 6: Purification of the Compound of Formula (VIII). Effect of the Invention

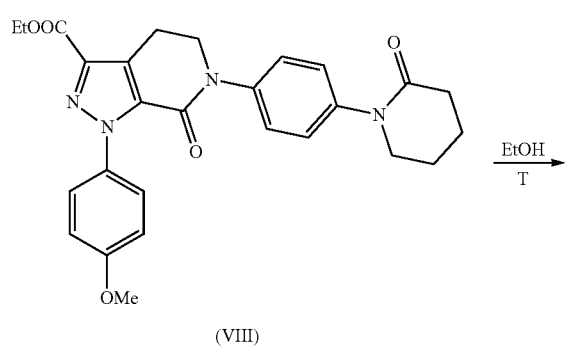

(VIII)

A 4-neck round bottom flask was charged with 10 g of ethyl 1-(4-methoxyphenyl)-7-oxo-6-(4-(2-oxopiperidin-1-yl)phenyl)-4,5,6,7-tetrahydro-1H-pyrazolo[3,4-c]pyridine-3-carboxylate (0.02 mol) (compound of formula (VIII)) containing 0.21% (HPLC A/A %) of dimer of formula (IV) and 0.10% (HPLC A/A %) of dimer impurity of formula (V).

Said compound was suspended in 100 mL of ethanol and the mixture is heated to reflux, resulting in an opalescent solution. Activated carbon was added (1 g) and, after additional 30 minutes at reflux, the mixture was filtered, while still hot, washing with pre-heated ethanol (2×20 mL). The filtered solution is cooled down to T=20/25° C. and stirred at this temperature for at least 2 hours. The slurry is then filtered washing the cake with ethanol (2×10 mL). The wet solid is dried under vacuum at T=65° C. The obtained 7.0 g of compound of formula (VIII) (70% molar yield) contained:

0.06% (HPLC A/A %) of (E)-diethyl 6,6'-(4,4'-(diazene-1,2-diyl)bis(4,1-phenylene))bis(1-(4-methoxyphenyl)-7-oxo-4,5,6,7-tetrahydro-1H-pyrazolo[3,4-c]pyridine-3-carboxylate) of formula (IV)

0.03% (HPLC A/A %) of (Z)-1,2-bis(4-(3-(ethoxycarbonyl)-1-(4-methoxyphenyl)-7-oxo-4,5-dihydro-1H-pyrazolo[3,4-c]pyridin-6(7H)-yl)phenyl)diazene oxide of formula (V).

Example 7: Purification of the Compound of Formula (VIII). Effect of the Invention

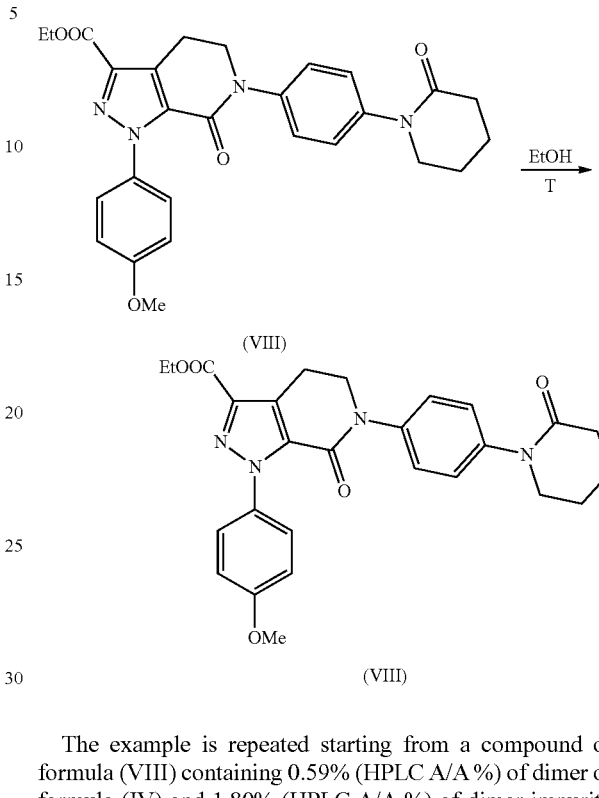

The example is repeated starting from a compound of formula (VIII) containing 0.59% (HPLC A/A %) of dimer of formula (IV) and 1.80% (HPLC A/A %) of dimer impurity of formula (V).

The obtained compound of formula (VIII) contained:
0.11% (HPLC A/A %) of dimer impurity of formula (IV)
0.36% (HPLC A/A %) of dimer impurity of formula (V).

Said compound (VIII) could be further purified repeating one or more times the procedure described in example 6.

Example 8

Analytic method for determining the amount of:
dimer impurity of formula (VI) and of formula (VII) in compounds of formula (IX) and (X),
dimer impurity of formula (IV) and of formula (V) in compound of formula (VIII)
dimer impurity of formula (II) and of formula (III) in Apixaban of formula (I)

Said compounds could be identified and monitored via the following HPLC method:

Chromatographic Conditions:

| Column: | XBridge C18 150 × 4.6 mm 3.5 μm |
| Temp. Column: | 40° C. |
| Quaternary System | |

| Mobile Phase A: | $H_2O$ MilliQ |
| Mobile Phase B: | Acetonitrile |
| Mobile Phase C: | Methanol |

| Gradient: | Time (min) | % A | % B | % C |
|---|---|---|---|---|
| | 0 | 75 | 15 | 10 |
| | 20 | 5 | 85 | 10 |
| | 25 | 5 | 85 | 10 |

-continued

| Binary System | |
|---|---|
| Mobile Phase A: | H$_2$O MilliQ/Methanol 90/10 |
| Mobile Phase B: | Acetonitrile/Methanol 90/10 |

| Gradient: | Time (min) | % A | % B |
|---|---|---|---|
| | 1 | 83.5 | 16.5 |
| | 21 | 5.5 | 94.5 |
| | 25 | 5.5 | 94.5 |
| Post run: | 7 min. | | |
| Flow: | 1.0 mL/min | | |
| Detector | UV a 243 nm | | |
| Injection Volume: | 5 μL | | |
| Run Time: | 25 min | | |
| Sample diluent: | CH$_2$Cl$_2$/EtOH/H$_2$O 1:5:4 | | |

Applying the conditions described above the expected retention times are as indicated below:

| Compound | RT | RRT |
|---|---|---|
| Compound of formula (IX) | 8.02 min | 1.14 |
| Compound of formula (X) | 4.70 min | 0.67 |
| Compound of formula (XI) | 6.30 min | 0.90 |
| Dimer Impurity of formula (VI) | 11.67 min | 1.66 |
| Dimer Impurity of formula (VII) | 11.10 min | 1.58 |
| Compound of formula (VIII) | 11.37 min | 1.62 |
| Dimer Impurity of formula (IV) | 18.31 min | 2.60 |
| Dimer Impurity of formula (V) | 17.75 min | 2.52 |
| Apixaban of formula (I) | 7.03 min | 1.00 |
| Dimer Impurity of formula (II) | 12.31 min | 1.75 |
| Dimer Impurity of formula (III) | 12.00 min | 1.71 |

The amounts of the dimer impurities described in description and examples for the compounds of formula (I), (VIII), (IX) and (X), in particulars in amounts expressed in HPLC A/A %, can be carried out according to the HPLC method described in this example 8.

LC-MS Method for Determination of Dimer Impurities of Apixaban.

| LC parameters | |
|---|---|
| Equipment: | Agilent 1100 Series LC/MSD Trap |
| Column: | Poroshell SB-C18 150 × 4.6 mm 2.7 μm |
| Temp. Column: | 40° C. |
| Mobile Phase A: | H$_2$O |
| Mobile Phase B: | Acetonitrile/Methanol 80/20 |

| Gradient: | Time (min) | % A | % B |
|---|---|---|---|
| | 0 | 85 | 15 |
| | 25 | 5 | 95 |
| | 30 | 5 | 95 |
| Flow: | 1.0 mL/min | | |
| Detector: | UV 243 nm | | |
| Injection Volume | 5 μL | | |
| Run Time: | 30 min | | |
| Post run | 5 min | | |

| MS parameters | |
|---|---|
| Polarity of MS: | positive |
| Ionization: | APCl |
| Nebulization pressure: | 60 psi |
| Drying gas flow: | 5 L/min |
| Drying gas temperature:: | 350° C. |
| Vap temperature | 400° C. |
| Corona current | 4000 nA |
| Capillary voltage | 3500 V |
| Mass Range: | 100-900 amu |

| Sample preparation | |
|---|---|
| Sample diluent: | CH$_2$Cl$_2$/EtOH/H$_2$O 1:5:4 |
| Sample concentration | 2 mg/mL |

Example 9: Preparation of the Dimer Impurity of Formula (IV) and the Dimer Impurity of Formula (V), Starting from a Mixture of the Dimer Impurity of Formula (VI) and the Dimer Impurity of Formula (VII)

Synthesis Scheme:

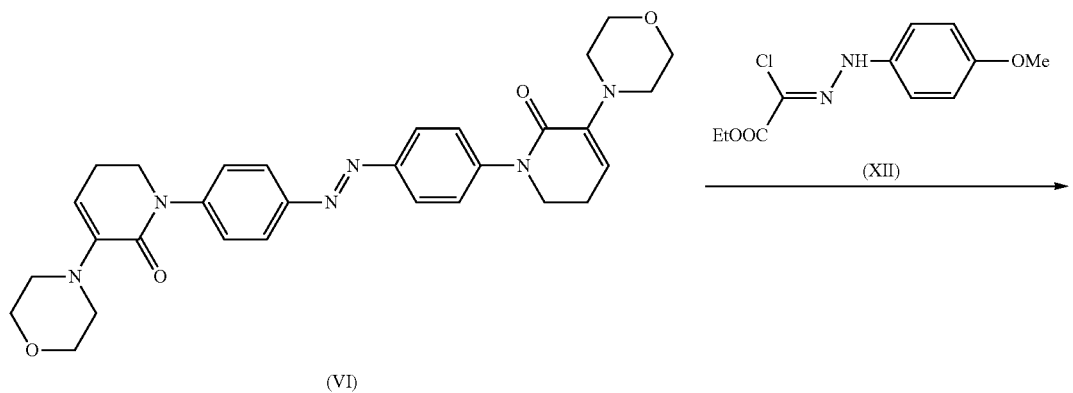

-continued
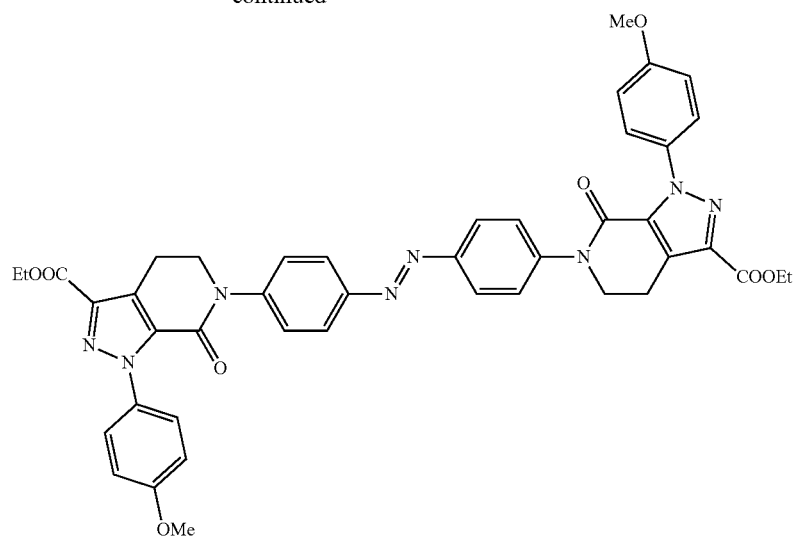
(IV)
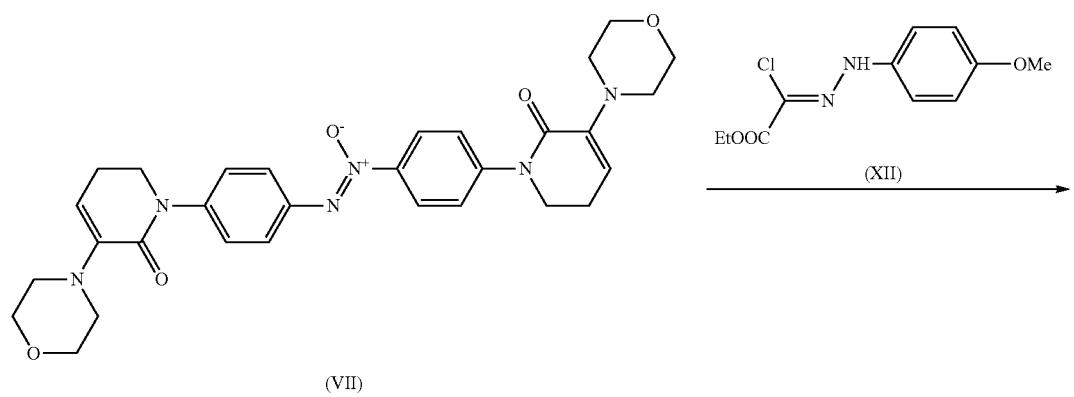
(VII)     (XII)
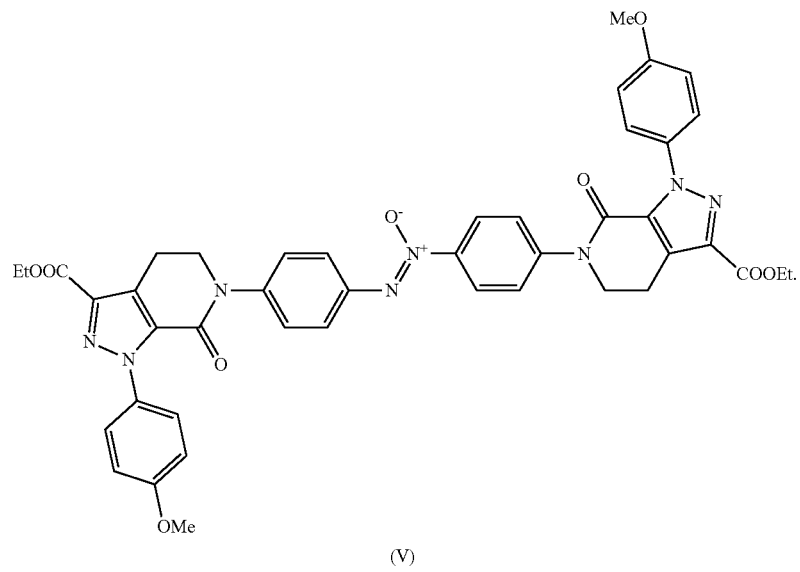
(V)

In a round bottom flask were charged: the mixture of dimer impurity of formula (VI) and dimer impurity of formula (VII) prepared reworking examples 2 and 3 at large scale (14 g, 25 mmol, 1.0 eq. considering the molecular weight of the dime impurity of formula (VII) species), the compound of formula (XII) (90 g, 350 mmol, 7.0 eq.), triethylamine (76 g, 750 mmol, 15.0 eq.), potassium iodide (8.5 g, 51 mmol, 1.0 eq.) and ethyl acetate (1960 ml). The suspension was heated to reflux and stirred for 16 hours, then cooled down to T=20/25° C. and filtered to remove the insoluble, washing the cake with ethyl acetate (3×20 ml).

To the resulting solution was slowly added at T=20/25° C. an aqueous 32% HCl solution (72 ml, d=1.16 g/ml) and the mixture is stirred for 30 minutes at this temperature.

The slurry was filtered and the collected wet solid was suspended in a sodium carbonate saturated solution (50 ml) at T=20/25° C. After 30 min stirring at this temperature, the mixture was filtered and the wet cake was washed with sodium carbonate saturated solution (50 ml) and then with water (20 ml).

Upon drying at reduced pressure and T=65° C. for 8 hours, 8.4 g of Dimer impurities mixture were obtained (40% yield, HPLC A %: Dimer of formula (V) (MW 824) 71.3%; Dimer of formula (IV) (MW 808) 12.2% HPLC A/A %.

Example 10: Preparation of the Dimer Impurity of Formula (V) and the Dimer Impurity of Formula (IV), Starting from the Dimer Impurity of Formula (III) and the Dimer Impurity of Formula (II)

Synthesis Scheme:

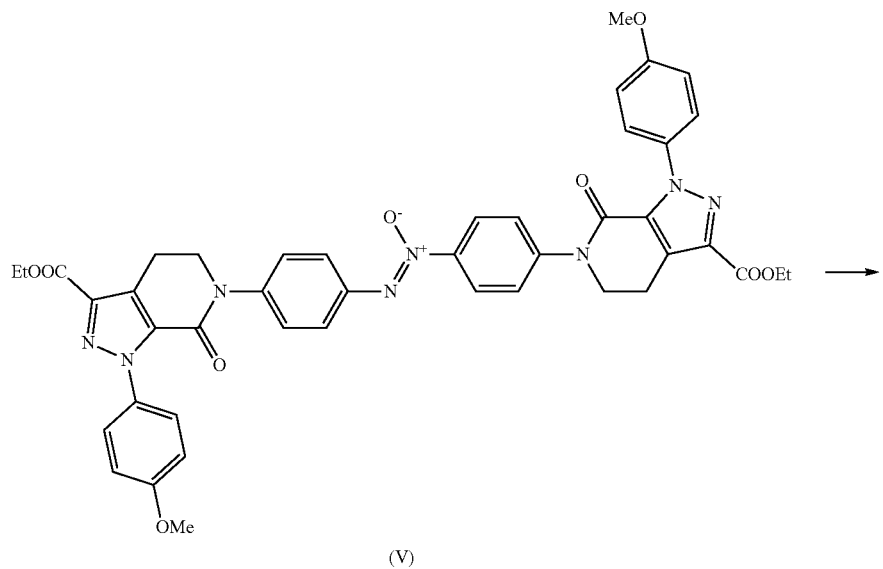

(V)

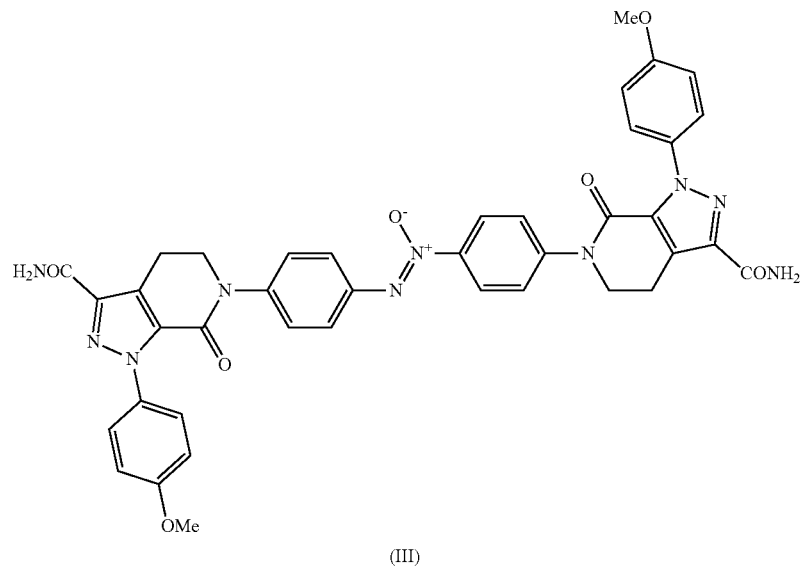

(III)

-continued

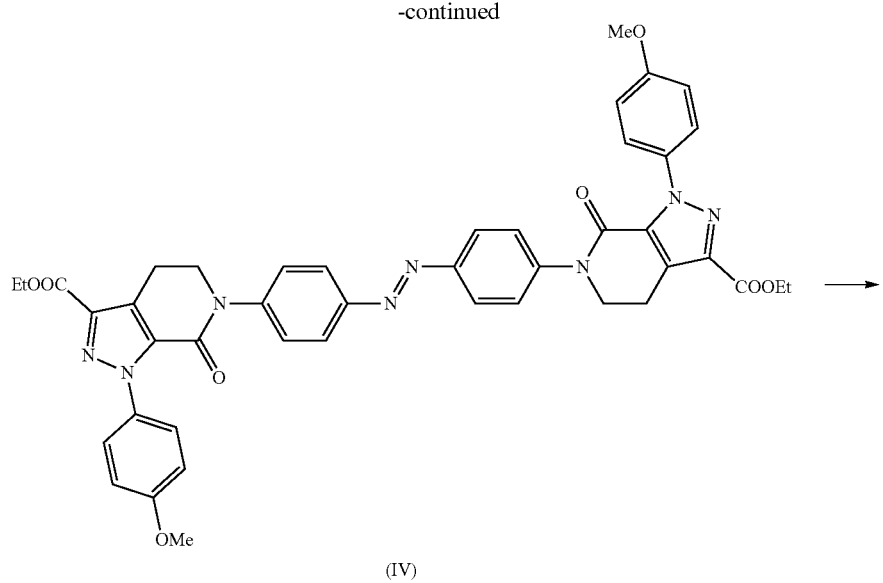

(IV)

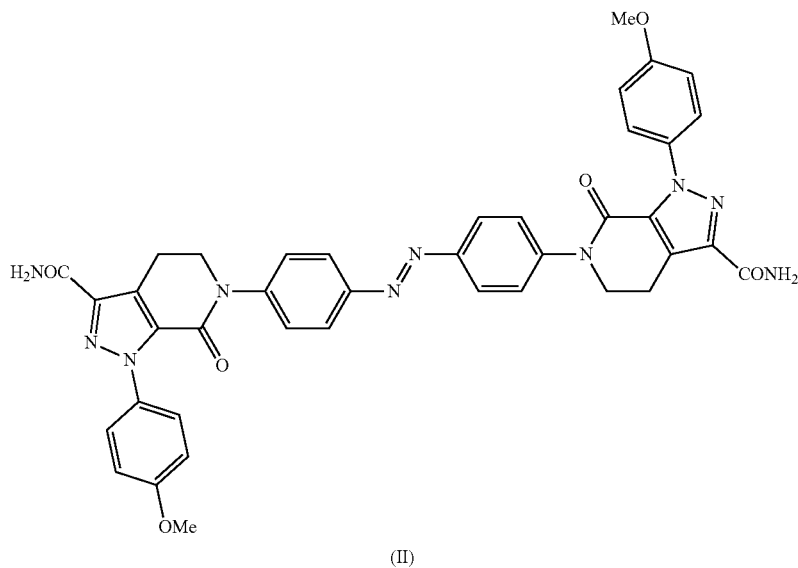

(II)

In a 1 L stainless steel autoclave were charged the mixture of dimer impurity of formula (IV) and dimer impurity of formula (V) from the example 9 carried out at large scale (15 g, 18.5 mmol, 1.0 eq. considering the molecular weight of the Dimer impurity of formula (V) MW 824 species) and propylene glycol (600 ml). After nitrogen purges, ammonia was charged up to a stable internal pressure of p=1.5/2.0 bar at T=20/25° C. The mixture was then heated to T=120° C. reaching an internal pressure of P=9 bars. After 40 hours at this temperature, the mixture was cooled to T=20/25° C. and diluted with propylene glycol (30 ml), water (360 ml) and ethanol (90 ml). The resulting slurry was stirred for 1 hour at T=20/25° C. and finally filtered washing the cake with water (60 ml). The wet material was dried at reduced pressure and T=65° C. for 8 hours, affording 10.3 g of Dimer impurities mixture (74% yield, HPLC A %: dimer of formula (III) MW 766 48.53%; dimer of formula (II) MW 750 34.6%).

Example 11: Chromatographic Separation of Dimer Impurities Mixture and Analytical Test of Single Impurity Analytic methods for separating the following methods of Dimer impurities and following characterization of each single dimer impurity:
1. the mixture of dimer impurity of formula (VI) and dimer impurity of formula (VII),
2. the mixture of dimer impurity of formula (IV) and dimer impurity of formula (V),
3. the mixture of dimer impurity of formula (II) and dimer impurity of formula (III).

1. Chromatographic Separation of the Mixture of Dimer Impurity of Formula (VI) and Dimer Impurity of Formula (VII).

The separation of said mixture, obtained in the example 3, was achieved via preparative HPLC (Agilent Technologies 1200 series) applying the following conditions:

Chromatographic Conditions:

| Column: | Zorbax-Rx-Sil, 21.2 × 250 mm, 7 µm |
|---|---|
| Temp. Column: | 25° C. |
| Mobile Phase A: | DCM |
| Mobile Phase B: | EtOH |

| Gradient: | Time (min) | % A | % B |
|---|---|---|---|
| | 0 | 97 | 3 |
| | 20 | 97 | 3 |
| Flow: | | 20 mL/min | |
| Detector | | UV a 220 nm | |
| Injection Volume: | | 300 µL | |
| Run Time: | | 20 min | |
| Sample diluent: | | $CH_2Cl_2$ | |
| Sample conc | | 5 mg/mL | |

Characterization of Dimer Impurity of Formula (VII).

Retention time: 11.8 min (obtained by means of the chromatographic conditions above described).

LC-MS (ESI+): m/z=559, [M+H]$^+$ $^1$H NMR (400 MHz, CDCl$_3$) δ (ppm): 8.34 (d, J=8.8 Hz, 2H); 8.27 (d, J=8.8 Hz, 2H); 7.51 (m, 4H); 5.73 (m, 2H); 3.85 (m, 12H); 2.93 (m, 8H); 2.56 (m, 4H). $^{13}$C and DEPT 135 NMR (100 MHz, CDCl$_3$) δ (ppm): 161.3 (C); 145.6 (C); 145.05 (C); 143.7 (C); 143.6 (C); 143.5 (C); 141.3 (C); 126.3 (CH); 124.6 (CH); 124.5 (CH); 122.7 (CH); 115.2 (CH); 114.9 (CH); 66.7 (CH$_2$); 50.5 (CH$_2$); 48.4 (CH$_2$); 23.4 (CH$_2$).

UV-Vis Spectrum:

maximum absorption at 350-360 nm.

Characterization of Dimer Impurity of Formula (VI).

Retention time: 14.3 min (obtained by means of the chromatographic conditions above described).

LC-MS (ESI+): m/z=543, [M+H]$^+$ $^1$H NMR (400 MHz, CDCl$_3$) δ (ppm): 8.00 (m, 4H); 7.56 (m, 4H); 5.37 (m, 2H); 3.73 (m, 12H); 3.27 (m, 8H); 2.96 (m, 4H).

2. Chromatographic Separation of the Mixture of Dimer Impurity of Formula (IV) and Dimer Impurity of Formula (V), The separation of said mixture, obtained in the example 9, was achieved via preparative HPLC (Agilent Technologies 1200 series) applying the following conditions:

Chromatographic Conditions:

| Column: | Zorbax-Rx-Sil, 21.2 × 250mm, 7 µm |
|---|---|
| Temp. Column: | 25° C. |
| Mobile Phase A: | DCM |
| Mobile Phase B: | EtOH |

| Gradient: | Time (min) | % A | % B |
|---|---|---|---|
| | 0 | 98 | 2 |
| | 10 | 98 | 2 |
| Flow: | | 20 mL/min | |
| Detector | | UV a 220 nm | |
| Injection Volume: | | 300 µL | |
| Run Time: | | 10 min | |
| Sample diluent: | | $CH_2Cl_2$ | |
| Sample conc | | 10 mg/mL | |

Characterization of Dimer Impurity of Formula (V).

Retention time: 3.0 min (obtained by means of the chromatographic conditions above described).

LC-MS (ESI+): m/z=825, [M+H]$^+$ $^1$H NMR (400 MHz, CDCl$_3$) δ (ppm): 8.32 (d, J=9.2 Hz, 2H); 8.24 (d, J=9.2 Hz, 2H); 7.48 (m, 8H); 6.95 (dd, J1=8.8 Hz J2=2 Hz, 4H); 4.49 (q, J=6.8 Hz, 4H); 4.21 (m, 4H); 3.84 (s, 6H); 3.36 (m, 4H); 1.46 (t, J=6.8 Hz, 6H).

$^{13}$C and DEPT 135 NMR (100 MHz, CDCl$_3$) (ppm): 162.1 (C); 162.0 (C); 160.0 (C); 159.9 (C); 157.1 (C); 145.5 (C); 144.7 (C); 142.5 (C); 141.7 (C); 139.1 (C); 139.0 (C); 126.94 (CH); 126.93 (CH); 126.4 (CH); 125.2 (CH); 125.1 (CH); 122.79 (CH); 113.73 (CH); 113.71 (CH); 61.33 (CH$_2$); 61.29 (CH$_2$); 55.5 (CH$_3$); 50.9 (CH$_2$); 21.6 (CH$_2$); 14.4 (CH$_3$);

UV-Vis Spectrum:

maximum absorption at 356-360 nm.

Characterization of dimer impurity of formula (IV).

Retention time: 4.0 min (obtained by means of the chromatographic conditions above described).

LC-MS (ESI+): m/z=809, [M+H]$^+$ $^1$H NMR (400 MHz, CDCl$_3$) (ppm): 7.94 (d, J=8.8 Hz, 4H); 7.50 (m, 8H); 6.95 (d, J=9.2 Hz, 4H); 4.49 (q, J=7.2 Hz, 4H); 4.22 (m, 4H); 3.84 (s, 6H); 3.36 (m, 4H); 1.46 (t, J=7.2 Hz, 6H).

UV-Vis Spectrum:

maximum absorption at 356-360 nm.

3. Chromatographic Separation of the Mixture of Dimer Impurity of Formula (II) and Dimer Impurity of Formula (III).

The separation of said mixture, obtained in the example 10, was achieved via preparative HPLC (Agilent Technologies 1200 series) applying the following conditions:

Chromatographic Conditions:

| Column: | Zorbax-Rx-Sil, 21.2 × 250 mm, 7 µm |
|---|---|
| Temp. Column: | 25° C. |
| Mobile Phase A: | DCM |
| Mobile Phase B: | i-PrOH |

| Gradient: | Time (min) | % A | % B |
|---|---|---|---|
| | 0 | 95 | 5 |
| | 20 | 95 | 5 |
| Flow: | | 20 mL/min | |
| Detector | | UV a 220 nm | |
| Injection Volume: | | 300 µL | |
| Run Time: | | 20 min | |
| Sample diluent: | | $CH_2Cl_2$ | |
| Sample conc: | | <5 mg/Ml | |
| | Due to the low solubility of the species, a 5 mg/mL solution was prepared and the insoluble filtered in order to obtain a clear solution | | |

Characterization of Dimer Impurity of Formula (III).

Retention time: 13.6 min (obtained by means of the chromatographic conditions above described).

LC-MS (ESI+): m/z=767, [M+H]$^+$ $^1$H NMR (400 MHz, CDCl$_3$) δ (ppm): 8.28 (d, J=9.2 Hz, 2H); 8.18 (d, J=8.8 Hz, 2H); 7.76 (bs, 2H); 7.63-7.52 (m, 8H); 7.47 (bs, 2H); 7.02 (d, J=8.8 Hz, 4H); 4.17 (m, 4H); 3.82 (s, 6H); 3.25 (m, 4H).

UV-Vis Spectrum: Shown in FIG. 4 maximum absorption at 360-370 nm.

Characterization of dimer impurity of formula (II).

Retention time: 14.6 min (obtained by means of the chromatographic conditions above described).

LC-MS (ESI+): m/z=751, [M+H]$^+$ $^1$H NMR (400 MHz, CDCl$_3$) (ppm): 7.93 (d, J=8.8 Hz, 4H); 7.76 (bs, 2H); 7.63-7.52 (m, 8H); 7.47 (bs, 2H); 7.02 (d, J=8.8 Hz, 4H); 4.17 (m, 4H); 3.82 (s, 6H); 3.25 (m, 4H).

UV-Vis Spectrum: Shown in FIG. 3 maximum absorption at 350-360 nm.

MS and UV spectra determination of Dimer Impurities

| LC parameters | | | |
|---|---|---|---|
| Equipment: | Agilent LC/MSD Trap SL | | |
| Column: | Poroshell SB-C18 150 × 4.6 mm 2.7 µm | | |
| Temp. Column: | 40° C. | | |
| Mobile Phase A: | TFA 0.1% (v/v) in H$_2$O | | |
| Mobile Phase B: | Acetonitrile/Methanol 80/20 | | |
| Gradient: | Time (min) | % A | % B |
| | 0 | 85 | 15 |
| | 25 | 5 | 95 |
| | 30 | 5 | 95 |
| Flow: | 1.0 mL/min | | |
| Detector: | UV 243 nm | | |
| Injection Volume | 5 µL | | |
| Run Time: | 30 min | | |
| Post run | 5 min | | |
| MS parameters | | | |
| Polarity of MS: | positive | | |
| Ionization: | ESI+ | | |
| Drying temp: | 320° C. | | |
| Nebulization pressure: | 70 psi | | |
| Drying gas flow: | 12 L/min | | |
| Trap Drive: | 42.9 | | |
| HV Capillary: | 4100 V | | |
| Current Capillary: | 40 nA | | |
| Mass Range: | 100-900 amu | | |
| Sample preparation | | | |
| Sample diluent: | CH$_2$Cl$_2$/EtOH/H$_2$O 1:5:4 | | |
| Sample concentration | 0.3 mg/mL | | |

In example 1, using prior art methods for the preparation of the compound of formula (IX), said compound was obtained having an high amount of dimers impurities of formula (VI) and (VII).

In example 2, applying the teaching of the present invention, i.e. filtering a solution of the compound (IX) in ethanol and water, the obtained compound of formula (IX) had a content of each dimer impurities of formula (VI) and (VII) lower than 0.10%.

By comparison of the example 1 and 2 can be thus highlighted the effect of the present invention relating to steps from a) to d).

In example 3 the impurities of formula (VI) and (VII) was prepared by the solid removed of the example 2, constituted by a mixture of the dimer impurities of formula (VI) and (VII).

Example 4 provide evidences that applying the method of the invention, the final product Apixaban comprises a content of dimer impurities of formula (II) and (III) lower than 0.10%.

Example 5 describes the preparation of the compound of formula (VIII) according to prior art methods and obtaining the compound (VIII) which comprises the dimer impurities of formula (IV) and (V) in high amounts, i.e. higher than 0.50% (HPLC A/A %).

Example 6 provided evidences of the effect of the invention since the compound (VIII) was purified according to the process of the invention, steps from e) to i), thus reducing the initial amount of impurities (IV) and (V) from 0.21% and 0.10% to respectively to 0.06% and 0.03%.

Example 7 provided again evidences of the effect of the invention since the compound (VIII) was purified according to the process of the invention, thus reducing the initial amount of impurities (IV) and (V) from 0.59% and 1.80% to respectively to 0.11% and 0.36% in the isolated compound (VIII). Obviously, the product (VIII) of this experiment can be further purified submitting it to the same experiment as described in example 6, and in the optional step h), one or more times.

Analysing the above experiments and results provided, especially considering the levels of dimers impurities in Apixaban, can be appreciated the effect provided by the process of the present invention in removing the dimer impurities thus providing Apixaban substantially free from dimer impurities.

The invention claimed is:
1. A method for the determining the presence of one or more dimer impurities selected from the group consisting of a compound of formula (II):

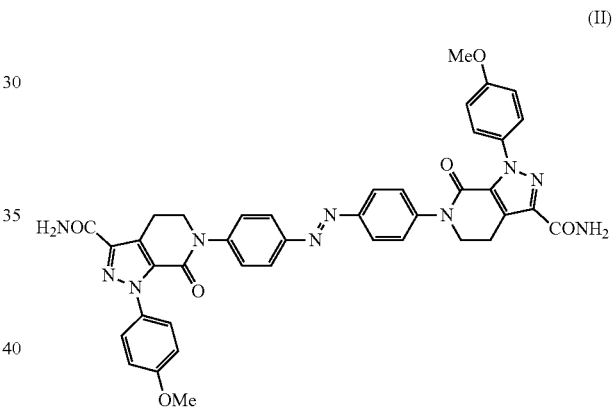

and the compound of formula (III):

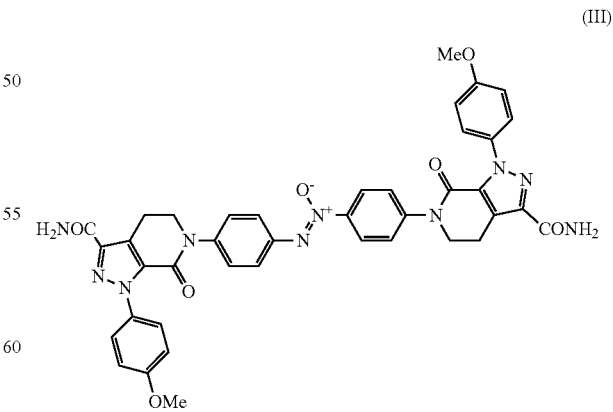

in an Apixaban sample comprising the steps of:
   a) combining a known amount of one or more dimer impurities selected from the group consisting of the compound of formula (II) and the compound of formula (III) to the Apixaban sample, b) carrying out HPLC or LC/MS analysis of the Apixaban sample of step a), and c) detecting the HPLC or LC/MS peak of the one or more dimer impurities of step a), or a1) analysing the one or more dimer impurities of step a) by HPLC or LC/MS, b1) analysing the Apixaban sample by HPLC or LC/MS, or c1) detecting the HPLC or LC/MS peaks corresponding with the one or more dimer impurities by comparing the retention times or relative retention times;

or detecting the peak having [M+1]$^+$ equal at 751 or 767 amu by LC/MS.

2. A method for the quantification of one or more dimer impurities selected from the group consisting of a compound of formula (II):

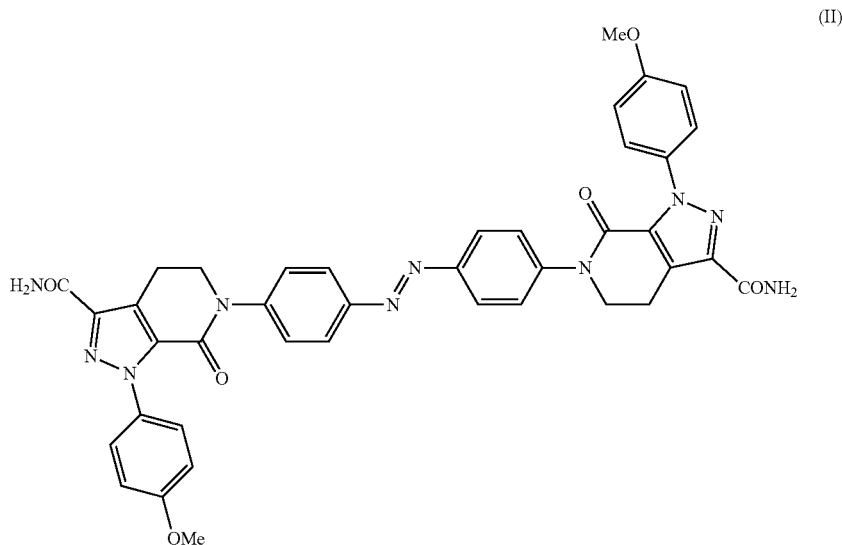 [SMILES: COc1ccc(-n2nc(C(N)=O)c3c2C(=O)N(c2ccc(/N=N/c4ccc(N5CCc6c(C(N)=O)nn(-c7ccc(OC)cc7)c6C5=O)cc4)cc2)CC3)cc1]

and the compound of formula (III):

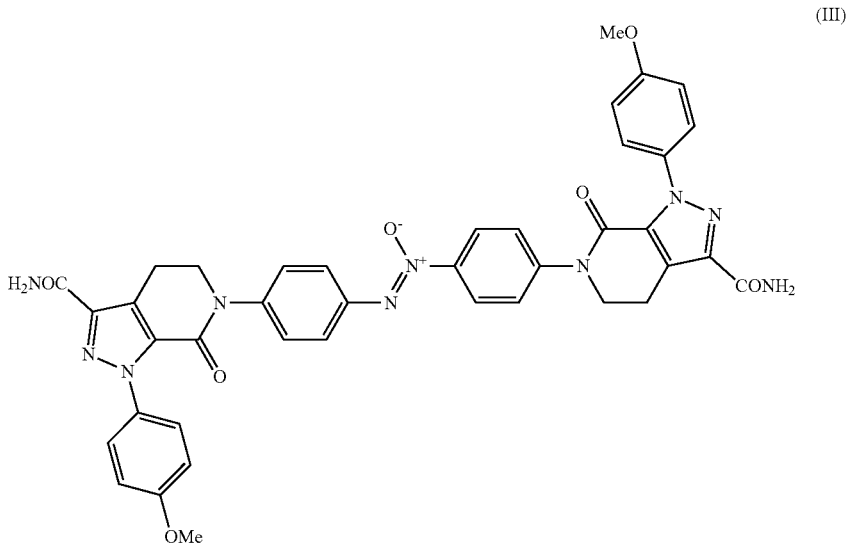 [SMILES: COc1ccc(-n2nc(C(N)=O)c3c2C(=O)N(c2ccc(/N=[N+](\[O-])c4ccc(N5CCc6c(C(N)=O)nn(-c7ccc(OC)cc7)c6C5=O)cc4)cc2)CC3)cc1]

in an Apixaban sample comprising the steps of:
  a) measuring the peak areas corresponding to the one or more dimer impurities in the Apixaban sample having an unknown amount of the one or more dimer impurities by HPLC or LC/MS,
  b) measuring the peak areas corresponding to a "reference standard" containing a known amount of the one or more dimer impurities by HPLC or LC/MS, and
  c) defining the amount of the one or more dimer impurities in the Apixaban sample by comparing the areas measured in step a) with those measured in step b).

3. The method according to claim 1, wherein the one or more dimer impurities is the compound of formula (III).

* * * * *